US006955856B2

(12) United States Patent
Lee et al.

(10) Patent No.: US 6,955,856 B2
(45) Date of Patent: Oct. 18, 2005

(54) BIPHENYL DERIVATIVES AND ORGANIC ELECTROLUMINESCENT DEVICE EMPLOYING THE SAME

(75) Inventors: Soo-hyoung Lee, Suwon-si (KR); Ji-hoon Lee, Chungju-si (KR); Sang-yeol Kim, Seoul (KR); Byung-hee Sohn, Yongin-si (KR); Jhun-mo Son, Yongin-si (KR)

(73) Assignee: Samsung SDI Co., Ltd., Gyeonggi-do (KR)

( * ) Notice: Subject to any disclaimer, the term of this patent is extended or adjusted under 35 U.S.C. 154(b) by 0 days.

(21) Appl. No.: 10/747,497

(22) Filed: Dec. 30, 2003

(65) Prior Publication Data

US 2004/0214040 A1 Oct. 28, 2004

(30) Foreign Application Priority Data

Dec. 30, 2002 (KR) ................. 10-2002-0087333

(51) Int. Cl.⁷ .......................... H05B 33/14; C09K 11/06
(52) U.S. Cl. ................. 428/690; 428/917; 313/504; 313/506; 564/433; 564/429; 548/440; 540/588; 544/102; 544/38; 546/101
(58) Field of Search ................. 428/690, 917; 313/504, 506; 564/433, 429; 548/440; 540/588; 544/38, 102; 546/101

(56) References Cited

U.S. PATENT DOCUMENTS 5,707,768 A * 1/1998 Anzai et al. ................. 430/71

FOREIGN PATENT DOCUMENTS

| JP | 63-235946 | | 9/1988 |
| JP | 01-142657 A | * | 6/1999 |
| WO | WO 02/15645 A1 | | 2/2002 |

* cited by examiner

Primary Examiner—Dawn Garrett
(74) Attorney, Agent, or Firm—Lee & Morse, P.C.

(57) ABSTRACT

A biphenyl derivative having an amino group with or without alkoxy substituent in the biphenyl backbone, and an organic electroluminescent device using the same.

9 Claims, 17 Drawing Sheets

(FORMULA 1C)

(FORMULA 1D)

(a)  (b)

BIPHENYL DERIVATIVES AND ORGANIC ELECTROLUMINESCENT DEVICE EMPLOYING THE SAME

BACKGROUND OF THE INVENTION

1. Field of the Invention

Embodiments of the present invention relate to biphenyl derivatives and an organic electroluminescent device using the same. More particularly, various embodiments of the invention pertain to biphenyl derivatives having alkoxy group(s) and substituted or unsubstituted amino group(s), and an organic electroluminescent device using the same. The electroluminescent device offers improved efficiency and emissive characteristics.

2. Description of the Related Art

An organic electroluminescent (EL) device is an active drive type emission display device that operates under the principle that when current is applied to fluorescent or phosphorescent organic compound layers (hereinafter "organic layers"), electrons and holes are combined in the organic layers to then electroluminesce. Organic electroluminescent devices have various advantages including being lightweight, simple components, having a simplified fabrication process, and offering a wide range of colors with high luminescence. Also, organic EL devices can enable moving picture display perfectly with high color purity, and the devices have electrical properties suitable for portable electronic devices at low power consumption and low driving voltage.

Such organic EL devices typically can be classified into low molecular weight organic EL devices and polymer EL devices depending on their materials.

Low molecular weight organic EL devices have advantages including the simple and easy synthesis and purification to a high degree of emissive compounds, and color pixels of the three primary colors can easily be obtained. However, since organic layers typically are formed by vacuum deposition, low molecular weight organic EL devices are difficult to be suitably applied for formation of large-area layers, in which spin coating or ink-jet printing is generally employed.

In polymer EL devices, thin layers can be formed easily by spin coating or printing, so that the polymer EL devices can be fabricated in a simplified manner, and can be fabricated easily into a large-screen size at low costs. However, such polymer-based EL devices have lower emission efficiency than low molecular weight EL devices, and they have experienced shortened lifetime characteristics due to deterioration of emissive polymer. Since defects that promote deterioration in molecular chains are generated during synthesis of such polymer materials and impurities are difficult to refine, it is difficult to obtain high-purity materials.

To address the problems of polymer-based EL devices while having advantages of both polymers and low molecular weight materials, there is a demand for development of new materials. That is, development of high-purity, high-efficiency materials which have high purity, high efficiency and satisfactory reproducibility in synthesis, which can easily attain a reproducible molecular design, and which are suitably applicable for a large-screen size, is highly requested.

The electroluminescence mechanism of a general organic EL device will now be described. Holes are moved from an anode to an emissive layer via a hole transport layer, and electrons are moved from a cathode to the emissive layer via an electron transport layer. The electrons and holes meet in the emissive layer for recombination, forming excitons. The excitons are subjected to radiative decay, producing light having a wavelength corresponding to a band gap of an emissive layer forming material.

Materials for forming the emissive layer usually are classified into fluorescent materials using singlet excitons and phosphorescent materials using triplet excitons according to the electroluminescence mechanism. Conventional organic EL devices generally use fluorescent materials using singlet excitons. In this case, approximately 75% of the energy of the produced singlet excitons is not utilized at all. Thus, in the case of using fluorescent materials as materials for forming an emissive layer, that is, in the case of using the fluorescence mechanism originating from the singlet excited state, the maximum internal quantum efficiency is approximately 25%. Further, since the refractive index of a substrate material is affected by light extraction efficiency, the actual external quantum efficiency is further reduced, that is, at most 5%. As far as phosphorescence from a singlet excited state is utilized, a reduction in the external quantum efficiency unavoidably occurs when the injected holes and electrons recombine in the emissive layer. Thus, various entities have attempted for a long time to enhance the emission efficiency utilizing a triplet excited state with 75% efficiency. However, a transition from a triplet excited state to a singlet ground state is forbidden; it is generally a non-radiative transition and there are some difficulties in utilizing the same.

Recently, EL devices that utilize phosphorescence through triplet excitons have been developed. Phosphorescent materials can be prepared by doping various metal complexes, e.g., Ir or Pt, into low-molecular weight hosts or polymer hosts. Examples of the metal complexes include an iridium complex [Ir $(ppy)_3$:tris(2-phenyl pyridine) iridium]. In the EL devices utilizing phosphorescent materials, efficiency, luminance, and lifetime characteristics thereof depend on the host material and the metal complex as a dopant. Therefore, the host material should be thermally, electrically stable.

Currently, 4,4'-N,N'-dicarbazole-biphenyl (CBP) is widely used as the host material. When an emissive layer is formed of CBP by vacuum deposition, an amorphous layer is homogenously formed. However, after performing vacuum deposition, the emissive layer may gradually lose homogeneity due to crystallization or coagulation, resulting in deterioration in emission efficiency and lifetime characteristics.

To manufacture highly efficient polymer EL devices that can overcome the problems, there is demand for development of new host materials having excellent crystal stability.

SUMMARY OF THE INVENTION

Various embodiments of the present invention provide biphenyl derivatives, substantially free of molecular defects, having improved thermal stability and crystal stability, that are easily purified, and easily capable of forming a thin layer using a soluble solvent. Embodiments of the present invention also provide an organic EL device with improved emission and efficiency characteristics by employing the biphenyl derivatives.

In accordance with a feature of an embodiment of the present invention, there is provided a biphenyl derivative represented by the following formula:

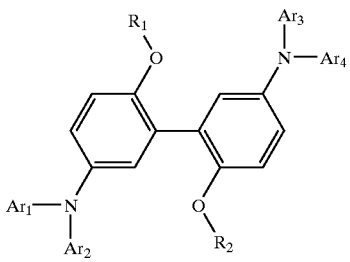

wherein $R_1$ and $R_2$ are independently a hydrogen; a $C_{1-20}$ linear or branched alkyl group; a $C_{5-20}$ cycloalkyl group; a $C_{6-20}$ aryl group; and a $C_{5-20}$ aryl group having at least one substituent selected from the group consisting of a halogen atom, a $C_{1-10}$ halogenated alkyl group, —Si(R)(R')(R''), a $C_{1-10}$ alkyl group, a $C_{1-10}$ alkoxy group, a $C_{6-10}$ aryl group, a $C_{4-10}$ heteroaryl group and —N(R)(R'), $Ar_1$, $Ar_2$, $Ar_3$ and $Ar_4$ are independently a hydrogen; a $C_{1-20}$ linear or branched alkyl group; a $C_{5-20}$ cycloalkyl group; a $C_{6-20}$ aryl group; and a $C_{6-20}$ aryl group having at least one substituent selected from the group consisting of a halogen atom, a $C_{1-10}$ halogenated alkyl group, —Si(R)(R')(R''), a $C_{1-10}$ alkyl group, a $C_{1-10}$ alkoxy group, a $C_{6-10}$ aryl group, a $C_{4-10}$ heteroaryl group and —N(R)(R'), where at least one selected from the group consisting of $Ar_1$ and $Ar_2$, and $Ar_3$ and $Ar_4$ can be interconnected, respectively, and R, R' and R'' are independently selected from the group consisting of a hydrogen atom, a $C_{1-10}$ alkyl group, a $C_{1-10}$ alkoxy group, a $C_{6-10}$ aryl group and a $C_{4-10}$ heteroaryl group.

In accordance with another feature of an embodiment of the present invention, there is provided an organic EL device comprising an organic layer between a pair of electrodes, the organic layer containing the above-mentioned biphenyl derivative.

BRIEF DESCRIPTION OF THE DRAWINGS

The above and other features and advantages of various embodiments of the present invention will become more apparent by describing in detail exemplary embodiments thereof with reference to the attached drawings in which.

DETAILED DESCRIPTION OF THE PREFERRED EMBODIMENTS

Figure 1A:
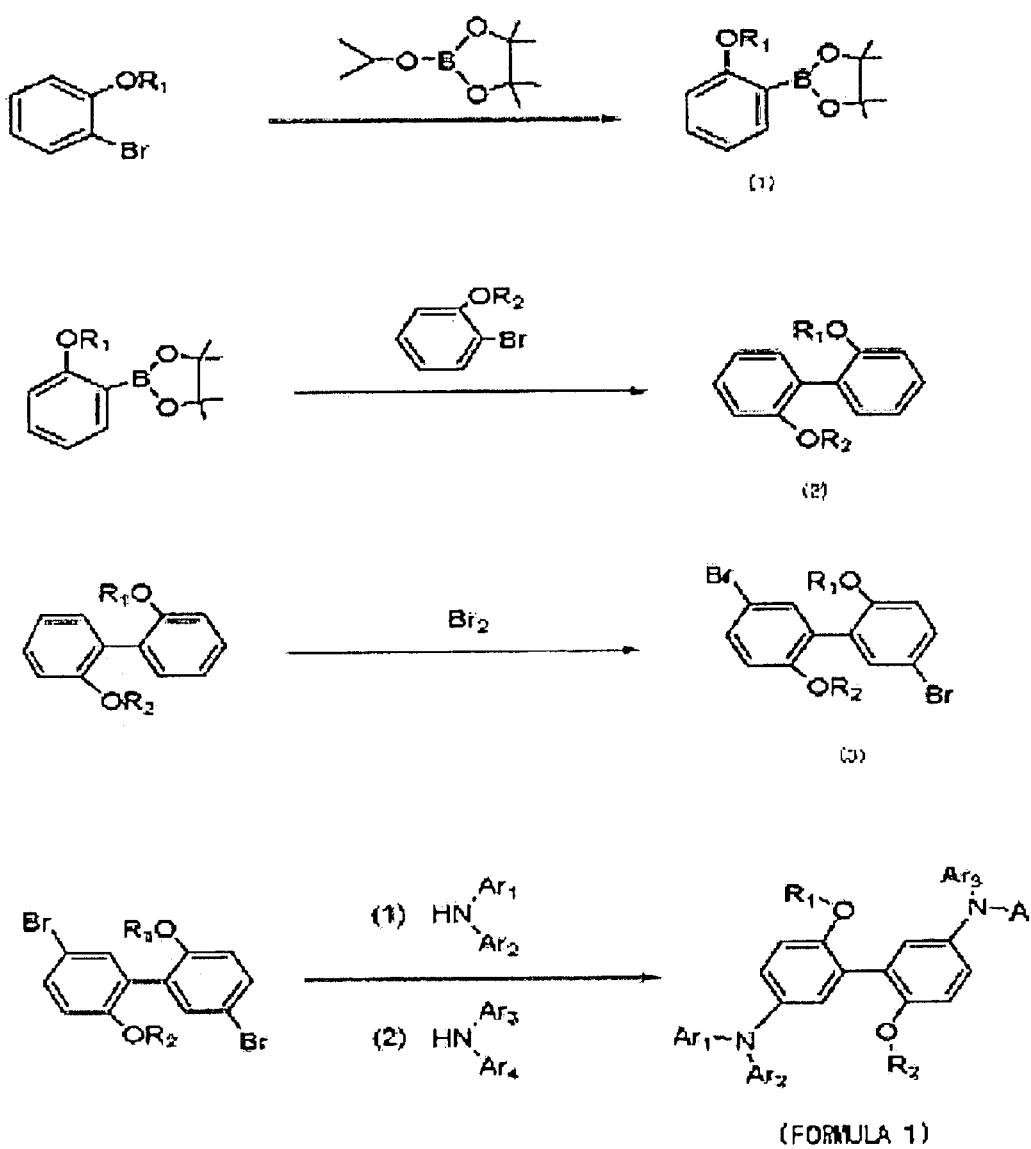
FIG. 1A is a reaction scheme illustrating the synthesis of a biphenyl derivative represented by formula 1 herein.

Korean Priority application No. 2002-87333, filed on Dec. 30, 2002, is incorporated herein in its entirety by reference.

The present invention will be described in detail below. A biphenyl derivative represented by formula 1 according to the present invention comprises a biphenyl derivative in its backbone and preferably has alkoxy groups introduced to the 2 and 2' positions of the biphenyl and substituted or unsubstituted amino groups at the 5 and 5' positions of the biphenyl in the biphenyl derivative, respectively:

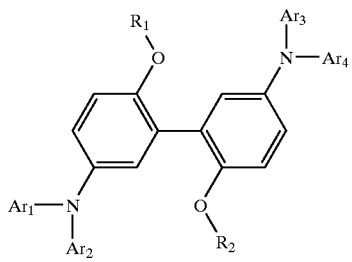

wherein: $R_1$ and $R_2$ are independently a hydrogen; a $C_{1-20}$ linear or branched alkyl group; a $C_{5-20}$ cycloalkyl group; a $C_{6-20}$ aryl group; and a $C_{6-20}$ aryl group having at least one substituent selected from the group consisting of a halogen atom, a $C_{1-10}$ halogenated alkyl group, —Si(R)(R')(R''), a $C_{1-10}$ alkyl group, a $C_{1-10}$ alkoxy group, a $C_{6-10}$ aryl group, a $C_{4-10}$ heteroaryl group and —N(R)(R');

$Ar_1$, $Ar_2$, $Ar_3$ and $Ar_4$ are independently a hydrogen; a $C_{1-20}$ linear or branched alkyl group; a $C_{5-20}$ cycloalkyl group; a $C_{6-20}$ aryl group; and a $C_{6-20}$ aryl group having at least one substituent selected from the group consisting of a halogen atom, a $C_{1-10}$ halogenated alkyl group, —Si(R)(R')(R''), a $C_{1-10}$ alkyl group, a $C_{1-10}$ alkoxy group, a $C_{6-10}$ aryl group, a $C_{4-10}$ heteroaryl group and —N(R)(R'), where at least one selected from the group consisting of $Ar_1$ and $Ar_2$, and $Ar_3$ and $Ar_4$ are interconnected, respectively; and R, R' and R'' are independently selected from the group consisting of a hydrogen atom, a $C_{1-10}$ alkyl group, a $C_{1-10}$ alkoxy group, a $C_{6-10}$ aryl group and a $C_{4-10}$ heteroaryl group.

Several disadvantages of the low molecular weight/polymer materials can be overcome by such a structural characteristic of the biphenyl derivative. In addition, various advantages of the low molecular weight/polymer materials, that is, free of molecular defects, easily purified, and easily capable of forming a thin layer using a soluble solvent, can be utilized in facilitating formation of a thin film. In particular, the biphenyl derivative represented by formula 1 has a twist structure so that the band gap between HOMO and LUMO energy levels is advantageously broad. A substituted or unsubstituted amino group having good hole transporting capability can be introduced to a para-position of an alkoxy group, thereby improving charge transporting capability. Thus, the biphenyl derivative can be used as a phosphorescent host material in an EL device utilizing a metal complex as a dopant.

The biphenyl derivative represented by formula 1 can be utilized as a material of a hole injection layer or a hole blocking layer as well as an emissive layer. In formula 1, —N(Ar$_1$)(Ar$_2$) and —N(Ar$_3$)(Ar$_4$) preferably are independently a group represented by formula 2 or 3, and more preferably a carbazole derivative group represented by formula 3:

<Formula 2>

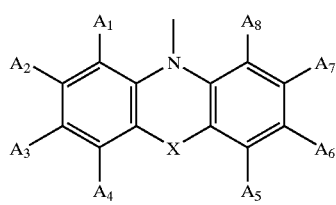

<Formula 3>

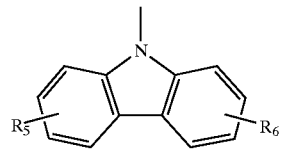

wherein X is a single bond or —(CH$_2$)$_n$—, where n is an integer of 1~2, —C(R$_3$)(R$_4$)—, —CH=CH—, —S—, —O— or —Si(R$_3$)(R$_4$)—, $A_1$, $A_2$, $A_3$, $A_4$, $A_5$, $A_6$, $A_7$, $A_8$, $R_3$, $R_4$, $R_5$ and $R_6$ are independently a hydrogen atom; a $C_{1-20}$ linear or branched alkyl group; a $C_{5-20}$ cycloalkyl group; a $C_{5-20}$ aryl group; and a $C_{5-20}$ aryl group having at least one substituent group selected from the group consisting of a halogen atom, a $C_{1-10}$ halogenated alkyl group, —Si(R)(R')(R''), a $C_{1-10}$ alkyl group, a $C_{1-10}$ alkoxy group, a $C_{6-10}$ aryl group, a $C_{4-10}$ heteroaryl group and —N(R)(R'), where at least one selected from the group consisting of $A_1$ and $A_2$, $A_2$ and $A_3$, $A_3$ and $A_4$, $A_5$ and $A_6$, $A_6$ and $A_7$, and $A_7$ and $A_8$ are interconnected, respectively, and R, R' and R'' are independently selected from the group consisting of a hydrogen, a $C_{1-10}$ alkyl group, a $C_{1-10}$ alkoxy group, a $C_{6-10}$ aryl group, and a $C_{4-10}$ heteroaryl group.

Examples of the group represented by formula 2 include groups (2a)

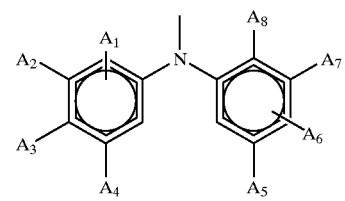

(2b)

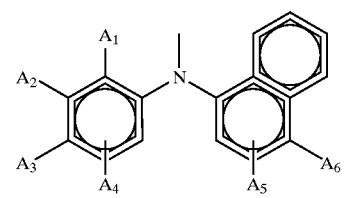

(2c)

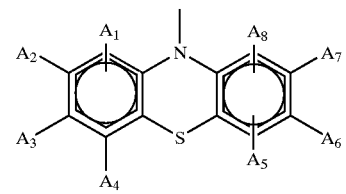

(2d)

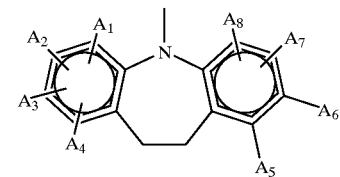

(2e)
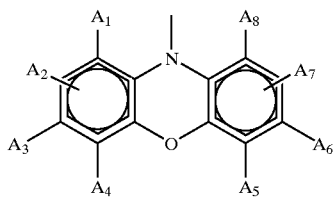

(2f)
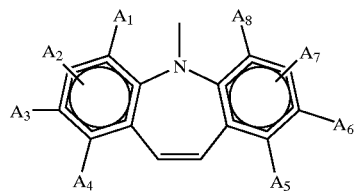

(2g)
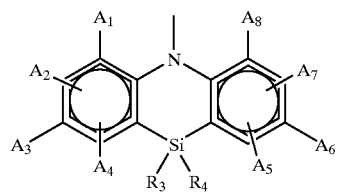

(2h)
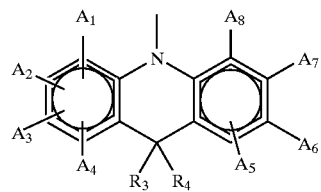

wherein $A_1$, $A_2$, $A_3$, $A_4$, $A_5$, $A_6$, $A_7$, $A_8$, $R_3$ and $R_4$ are as defined as above. In formula 3, $R_5$ and $R_6$ are preferably a group represented by formula 4:

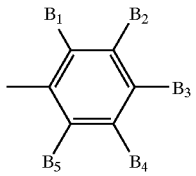

<Formula 4> wherein $B_1$, $B_2$, $B_3$, $B_4$ and $B_5$ are independently a hydrogen; a $C_{1-20}$ linear or branched alkyl group; a $C_{5-20}$ cycloalkyl group; a $C_{6-20}$ aryl group; and a $C_{6-20}$ aryl group having at least one substituent selected from the group consisting of a halogen atom, a $C_{1-10}$ halogenated alkyl group, —Si(R)(R')(R"), a $C_{1-10}$ alkyl group, a $C_{1-10}$ alkoxy group, a $C_{6-10}$ aryl group, a $C_{4-10}$ heteroaryl group and —N(R)(R'), R, R' and R" being independently selected from the group consisting of a hydrogen, a $C_{1-10}$ alkyl group, a $C_{1-10}$ alkoxy group, a $C_{6-10}$ aryl group, and a $C_{4-10}$ heteroaryl group.

Preferred examples of the biphenyl derivative represented by formula 1 include compounds represented by formulas 1a through 1e:

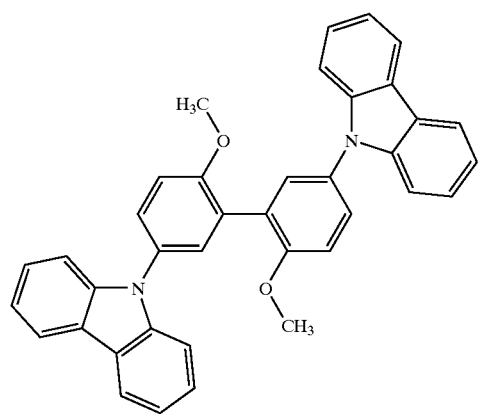

<Formula 1a>

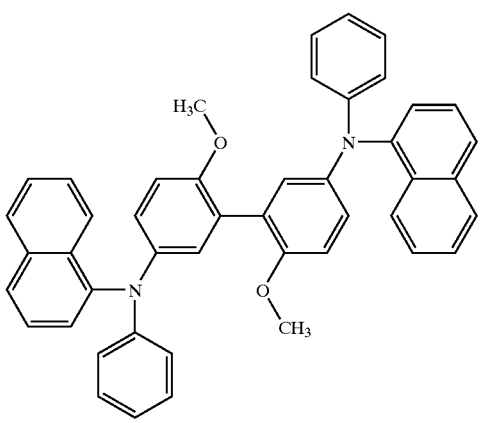

<Formula 1b>

<Formula 1c>

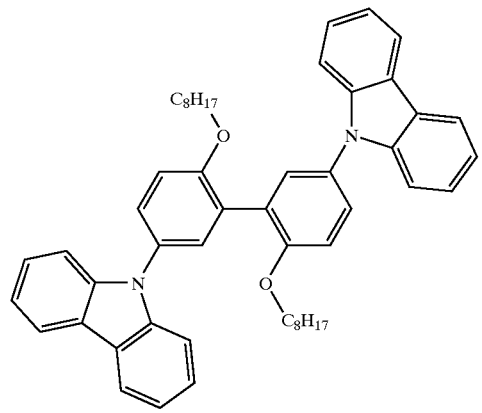

<Formula 1d>

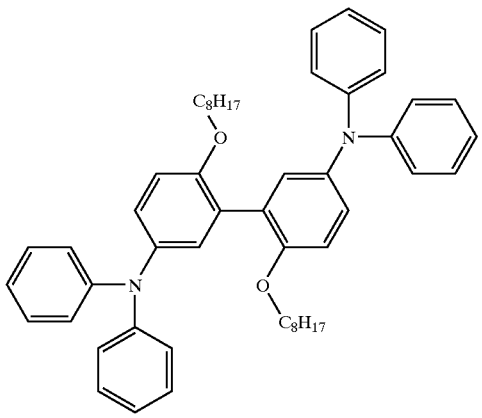

<Formula 1e>

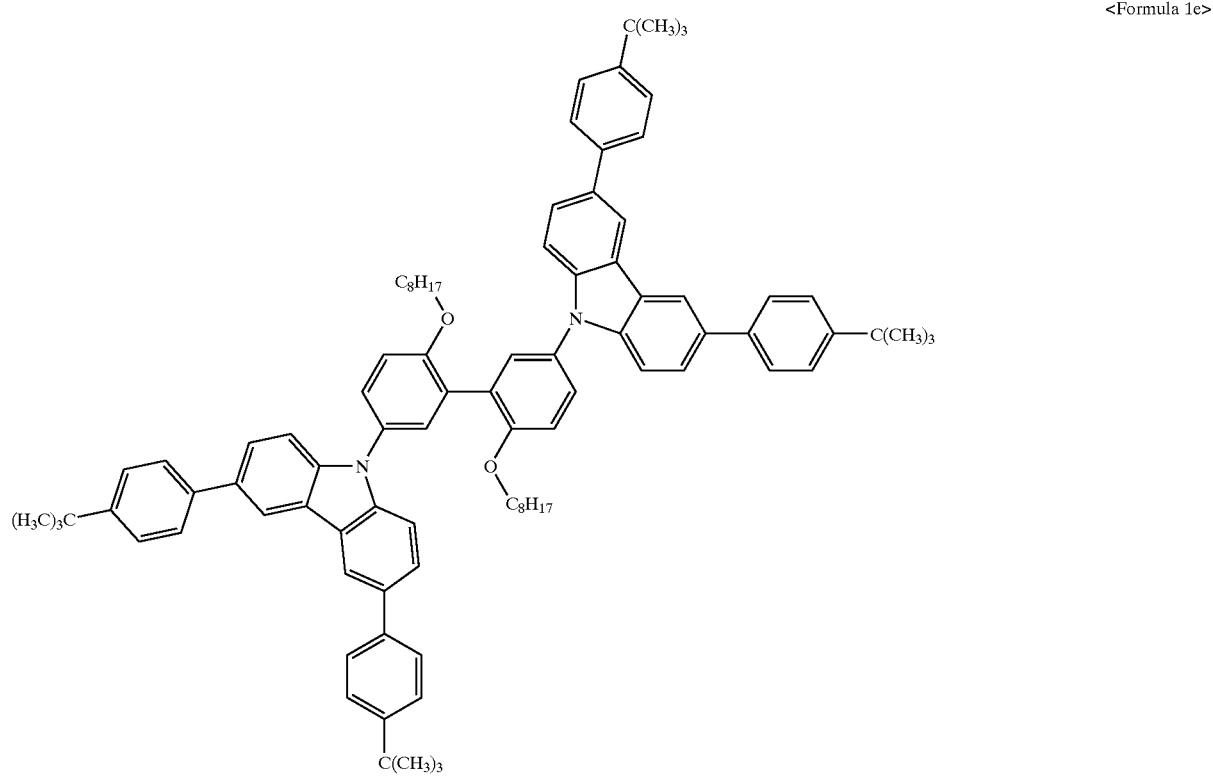

A method of synthesizing the biphenyl derivative represented by formula 1 is shown in FIG. 1, and an explanation thereof will follow.

After an alkoxy halogen compound was dissolved in a solvent such as THF, the mixture was cooled to a temperature in the range of 25 to −78° C., preferably to approximately −75° C., and n-butyl lithium was added thereto slowly. To this was added 2-isopropoxy-4,4,5,5-tetramethyl-1,3,2-dioxaborolane, thereby preparing an alkoxy boron compound (1).

Subsequently, the alkoxy boron compound (1) preferably was reacted with an alkoxy halogen compound in the presence of palladium (Pd) catalyst to prepare a biphenyl compound (2). The biphenyl compound (2) preferably was reacted with a halide to prepare a compound (3). Usable examples of the halide include bromine ($Br_2$) and iodine ($I_2$). The compound (3) then preferably was reacted with an amine compound in the presence of a Pd catalyst, thereby producing a biphenyl derivative represented by formula (1).

An organic electroluminescent (EL) device employing the biphenyl derivative represented by formula 1 according to various embodiments of the present invention and a manufacturing method thereof will now be described.

FIGS. 2A through 2F are views schematically illustrating various laminated structures of organic electroluminescent (EL) devices manufactured in examples herein.

Figure 2A:
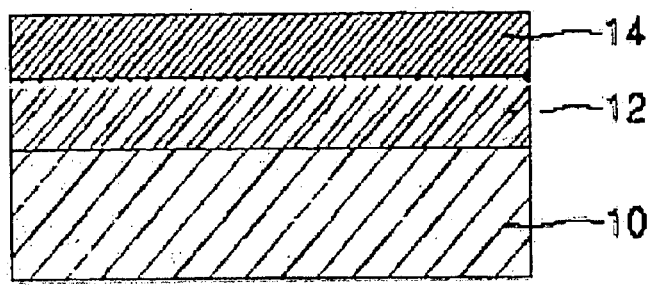
FIGS. 2A through 2F are views schematically illustrating laminated structures of organic electroluminescent (EL) devices manufactured in examples of embodiments of the present invention.

Referring to FIG. 2A, an emissive layer 12 having the biphenyl derivative represented by formula 1 is laminated on a first electrode 10, and a second electrode 14 is formed on the emissive layer 12.

Figure 2B:
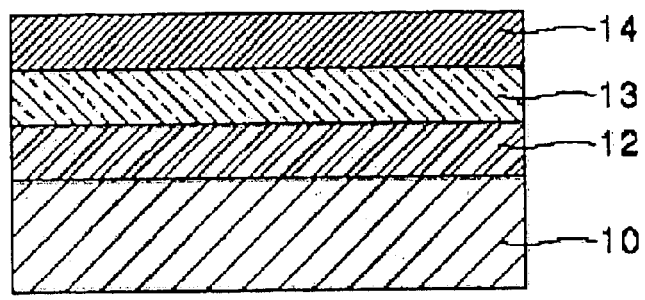

Referring to FIG. 2B, an emissive layer 12 having the biphenyl derivative represented by formula 1 preferably is laminated on a first electrode 10, a hole blocking layer (HBL) 13 is laminated on the emissive layer 12, and the second electrode 14 is formed on the HBL 13.

Figure 2C:
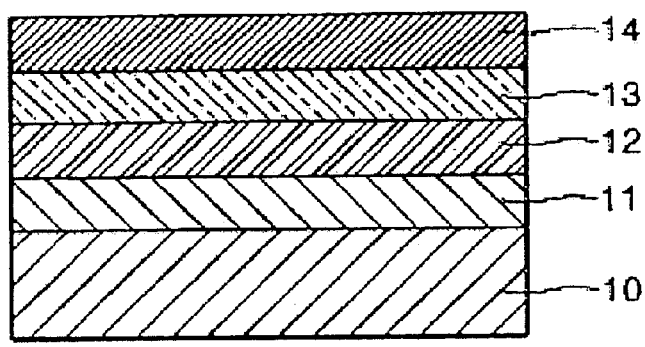
Figure 2D:
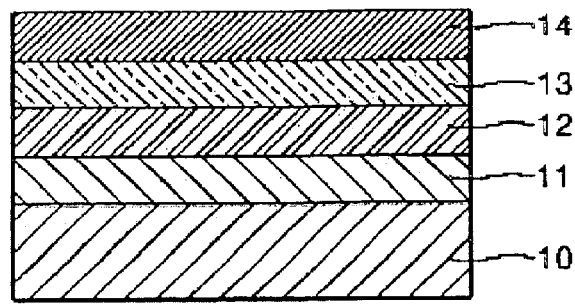

Referring to FIG. 2C, a hole injection layer (HIL) 11 preferably is formed between the first electrode 10 and the emissive layer 12. The organic EL device shown in FIG. 2D has essentially the same basic laminated structure as that shown in FIG. 2C except that an electron transport layer (ETL) 15, instead of the HBL 13, is formed on the emissive layer 12.

Figure 2E:
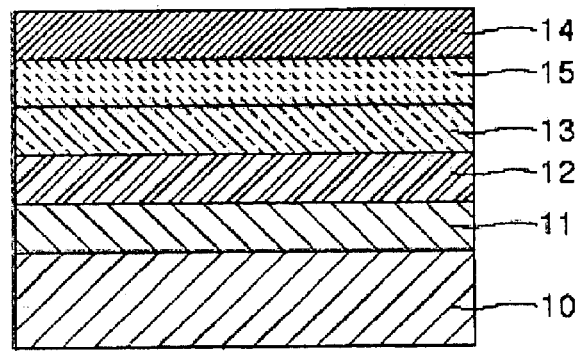

The organic EL device shown in FIG. 2E essentially has the same basic laminated structure as that shown in FIG. 2C except that a dual layer having a HBL 13 and an ETL 15 sequentially laminated, instead of the HBL 13, is formed on the emissive layer 12 having the biphenyl derivative represented by formula 1. In some cases, an electron injection layer may be further formed between the ETL 15 and the second electrode 14.

Figure 2F:
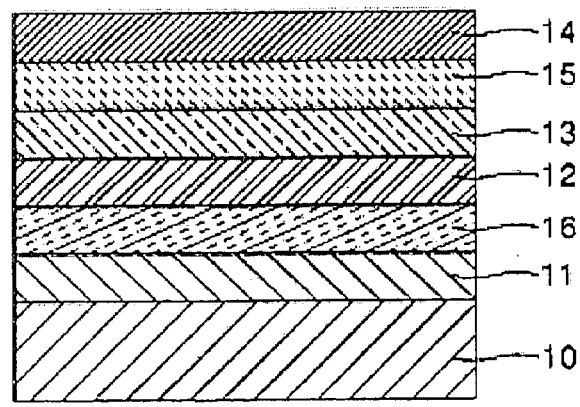

The organic EL device shown in FIG. 2F essentially has the same basic laminated structure as that shown in FIG. 2E except that a hole transport layer (HTL) 16 is further formed between the HIL 11 and the emissive layer 12. Here, the HTL 16 is believed to help prevent impurities from infiltrating from the HIL 11 to the emissive layer 12.

The organic EL device according to embodiments of the present invention can be manufactured by, but not limited to, conventional methods. Those skilled in the art will be capable of manufacturing an organic EL device using the guidelines provided herein.

A method of manufacturing an organic EL device according to a preferred embodiment of the present invention will now be described. First, a first electrode 10 is patterned on a substrate (not shown). The substrate preferably is a substrate used in a conventional organic EL device, more preferably a glass substrate or a transparent plastic substrate, which is transparent and has surface smoothness, manageability and waterproofness. Examples of the substrate include a glass substrate, a polyethyleneterephthalate substrate, a polycarbonate substrate and polyimide substrate. The substrate preferably has a thickness of from about 0.3 to about 1.1 mm.

Any material commonly used in the field can be used for the first electrode 10. In the case where the first electrode 10 is a cathode, it preferably is made of a conductive metal or an oxide thereof that is capable of easily injecting holes or an oxide thereof. Preferred materials for the first electrode 10 include, but are not limited to, ITO (Indium Tin Oxide), IZO (Indium Zinc Oxide), nickel (Ni), platinum (Pt), gold (Au) and iridium (Ir).

The substrate having the first electrode 10 preferably is cleaned and UV/$O_3$ treatment then is performed. In cleaning the substrate, an organic solvent such as isopropanol (IPA) or acetone can be used.

A hole injection layer 11 then preferably is selectively formed on the first electrode 10 of the cleaned substrate. Forming the hole injection layer 11 in such a manner is believed to increase contact resistance between the first electrode 10 and the emissive layer 12, and is believed to improve the hole transporting capability of the first electrode 10 with respect to the emissive layer 12, thereby improving the driving voltage and lifetime characteristic of a device. Any material commonly used in the field can be employed as the hole injection layer 11. Preferred materials for the hole injection layer 11 include, but are not limited to, PEDOT {poly(3,4-ethylenedioxythiophene)}/PSS(polystyrene parasulfonate), starburst materials, copper phthalocyanine, polythiophene, polyaniline, polyacetylene, polypyrrole, polyphenylene vinylene, or derivatives of these compounds, and m-MTDATA (4,4',4"-tris[N-(3-methylphenyl)-N-phenylamino]triphenylamine). The hole injection layer 11 can be spin-coated on the first electrode 10 and dried, thereby forming a hole injection layer 11. The hole injection layer 11 preferably has a thickness of from about 300 to about 2000 Å, more preferably 500–1100 Å. If the thickness of the hole injection layer 11 is not the range specified above, hole injection capability may be undesirably poor. The drying preferably is performed at a temperature within the range of from about 100 to about 250° C.

The emissive layer 12 preferably is formed by spin-coating an emissive layer forming composition on the hole injection layer 11 and drying. The emissive layer forming composition preferably comprises from about 0.5 to about 5% by weight of biphenyl derivative represented by formula 1 as an emissive material and from about 95 to about 99.5% by weight of a solvent. Any material that can dissolve the emissive material can be used as the solvent, and suitable examples thereof include toluene and chlorobenzene.

In some cases, a dopant may further be added to the emissive layer forming composition. The amount of the dopant may vary, preferably ranging from about 0.1 to about 30% by weight based on about 70 to about 99.9% by weight of the biphenyl derivative represented by formula 1. If the amount of the dopant is not within the range defined above, the emission characteristics of the EL device may undesirably deteriorate. Any material can be used for the dopant, including metal complexes exemplified by Ir(ppy)3, platinum octaethylporphine (PtOEP).

Preferably, the thickness of the emissive layer 12 is adjusted to be within the range of from about 100 to about 1000 Å, more preferably from about 500 to about 1000 Å, by adjusting the concentration of the emissive layer forming composition and the spin speed during spin coating. If the thickness of the emissive layer 12 is less than 100 Å, emission efficiency may be lowered. If the thickness of the emissive layer 12 is greater than 1000 Å, the driving voltage may undesirably increases.

A hole transport layer 16 may be selectively formed between the hole injection layer 11 and the emissive layer 12. Any material having hole transporting capability can be used, and examples thereof include PEDOT, polyaniline and polytriphenylamine. The thickness of the hole transport layer preferably is within the range of from about 100 to about 1000 Å.

A hole blocking layer 13 and/or an electron transport layer 15 may be formed on the emissive layer 12 by vapor-deposition or spin coating. The hole blocking layer 13 preferably prevents excitons formed from an emissive material from migrating to the electron transport layer 15 or prevents holes from migrating to the electron transport layer 15.

Examples of materials for forming the hole blocking layer 13 include TAZ (3-phenyl-4-(1'-naphthyl)-5-phenyl-1,2,4-triazole), BCP (2,9-dimethyl-4,7-biphenyl-1,10-phenanthroline), LiF, $MgF_2$, phenanthroline-based compounds, e.g., BCP manufactured by UDC Co., Ltd., imidazoles, triazoles, oxadiazoles, e.g., PBD, aluminum complexes manufactured by UDC Co., Ltd., BAlq (Aluminum(III) bis(2-methyl-8-quinolinato)4-phenylpheolate) represented by the following formula:

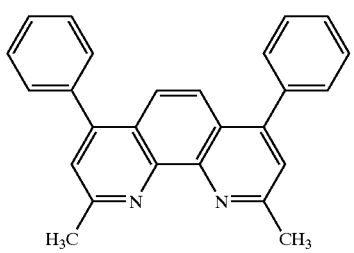

Phenanthroline-containing Organic Compound

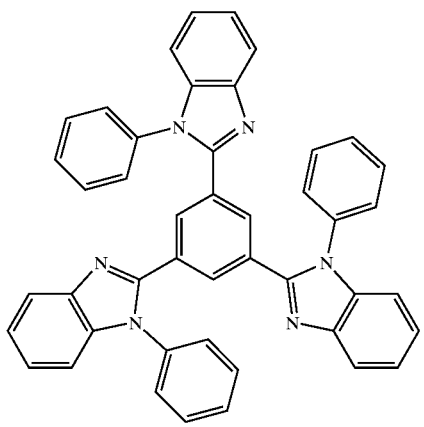

Imidazole-containing Organic Compound

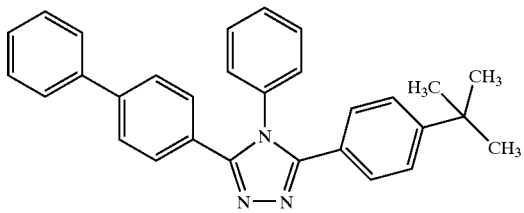

Triazole-containing Organic Compound

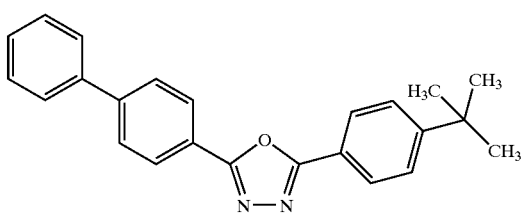

Oxidiazole-containing Organic Compound

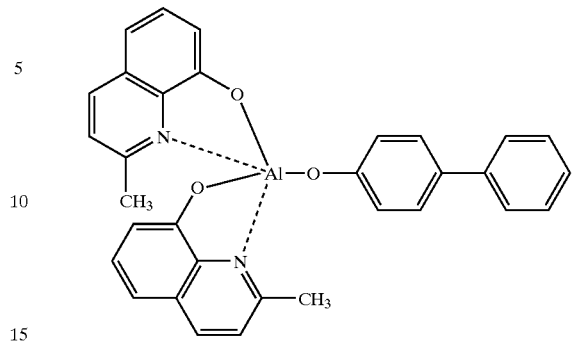

BAlq

Examples of materials useful for forming the electron transport layer 15 include oxazoles, isooxazoles, triazoles, isothiazoles, oxadiazoles, thiadiazoles, perylenes, aluminum complexes, e.g., Alq3 (tris(8-quinolinolato)-aluminum), BAlq, SAlq, or Almq3, and gallium complexes, e.g., Gaq'2OPiv, Gaq'2OAc or 2(Gaq'2).

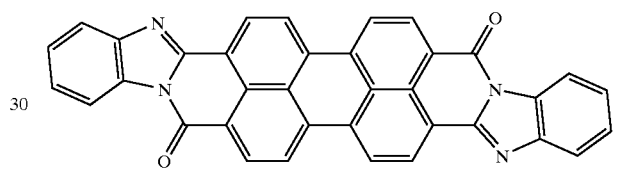

Perylene Compound

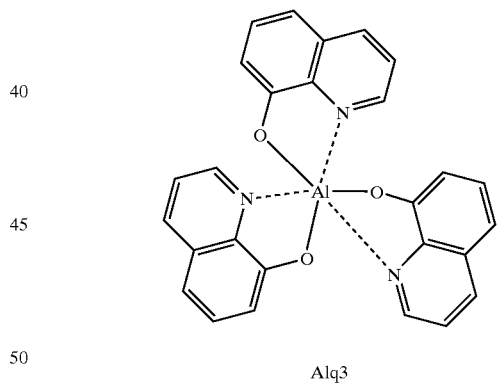

Alq3

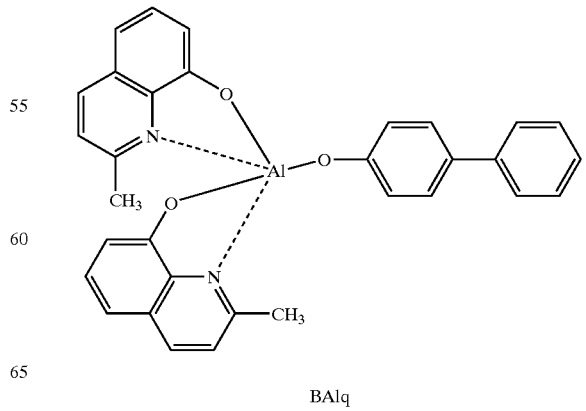

BAlq

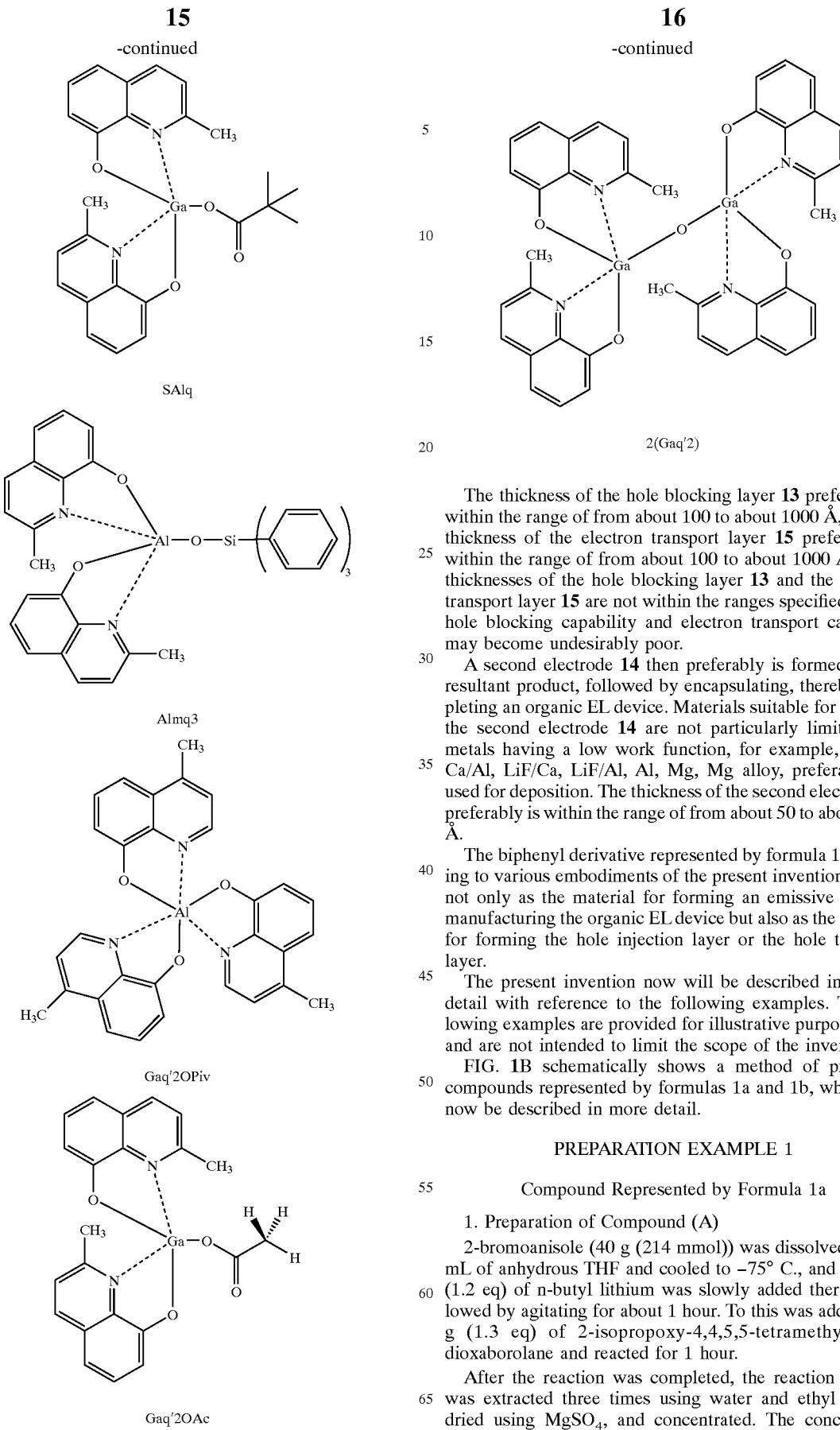

The thickness of the hole blocking layer 13 preferably is within the range of from about 100 to about 1000 Å, and the thickness of the electron transport layer 15 preferably is within the range of from about 100 to about 1000 Å. If the thicknesses of the hole blocking layer 13 and the electron transport layer 15 are not within the ranges specified above, hole blocking capability and electron transport capability may become undesirably poor.

A second electrode 14 then preferably is formed on the resultant product, followed by encapsulating, thereby completing an organic EL device. Materials suitable for forming the second electrode 14 are not particularly limited, and metals having a low work function, for example, Li, Ca, Ca/Al, LiF/Ca, LiF/Al, Al, Mg, Mg alloy, preferably are used for deposition. The thickness of the second electrode 14 preferably is within the range of from about 50 to about 3000 Å.

The biphenyl derivative represented by formula 1 according to various embodiments of the present invention is used not only as the material for forming an emissive layer in manufacturing the organic EL device but also as the material for forming the hole injection layer or the hole transport layer.

The present invention now will be described in greater detail with reference to the following examples. The following examples are provided for illustrative purposes only and are not intended to limit the scope of the invention.

Figure 1B:
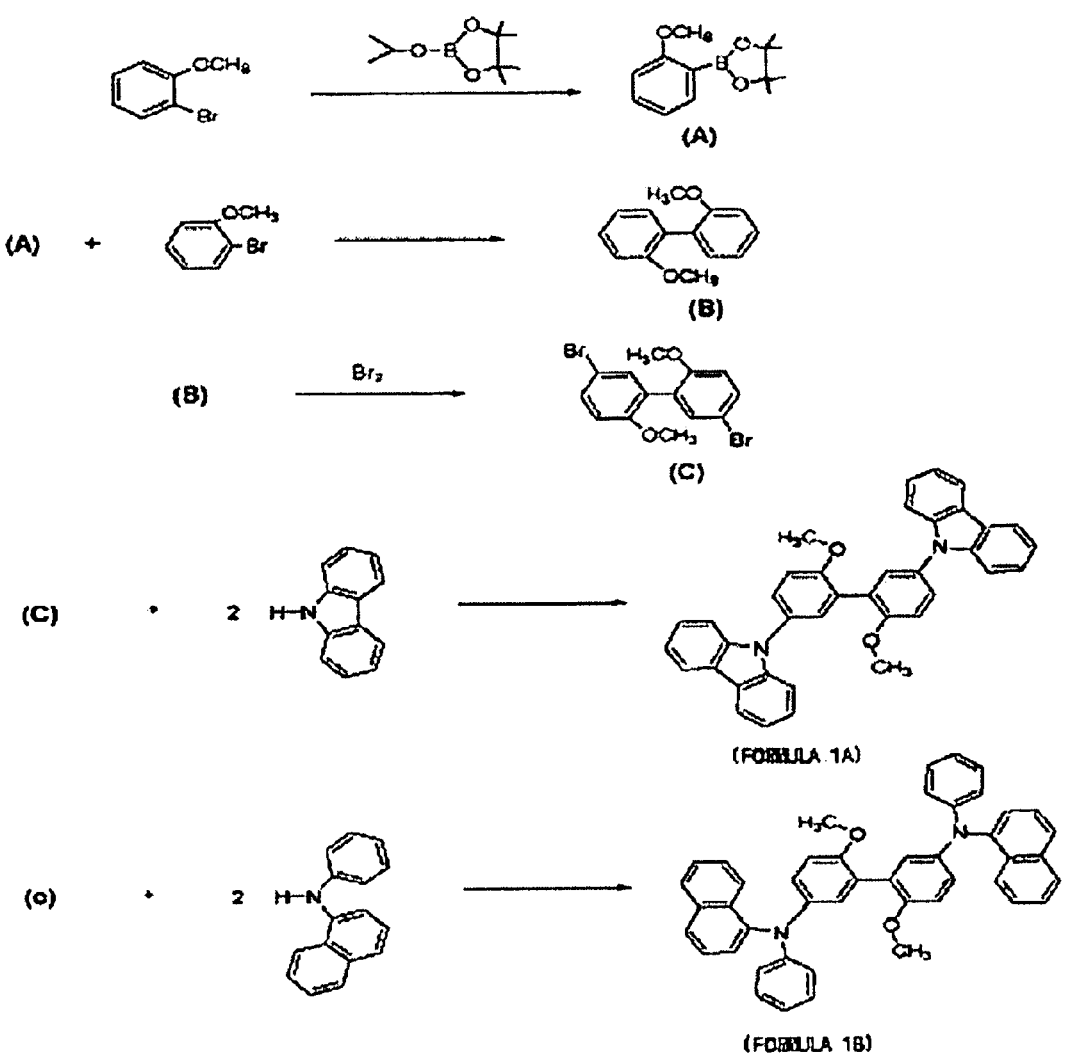
FIG. 1B is a reaction scheme illustrating the synthesis of compounds represented by formulas 1a and 1b according to Synthesis examples 1 and 2 herein.

FIG. 1B schematically shows a method of preparing compounds represented by formulas 1a and 1b, which will now be described in more detail.

PREPARATION EXAMPLE 1

Compound Represented by Formula 1a

1. Preparation of Compound (A)

2-bromoanisole (40 g (214 mmol)) was dissolved in 246 mL of anhydrous THF and cooled to −75° C., and 103 mL (1.2 eq) of n-butyl lithium was slowly added thereto, followed by agitating for about 1 hour. To this was added 51.8 g (1.3 eq) of 2-isopropoxy-4,4,5,5-tetramethyl-1,3,2-dioxaborolane and reacted for 1 hour.

After the reaction was completed, the reaction mixture was extracted three times using water and ethyl acetate, dried using MgSO$_4$, and concentrated. The concentrated product was subjected to distillation under reduced pressure to remove unreacted 2-isopropoxy-4,4,5,5-tetramethyl-1,3,2-dioxaborolane to produce the compound (A). The structure of the compound (A) was identified through $^1$H-NMR.

2. Preparation of Compound (B)

Compound (A) (10.3 g (44 mmol)) and 7.5 g (1.1 eq) of 2-bromoanisole were dissolved in 29 mL of anhydrous toluene, 29 mL of THF, and 89 mL of 2M $Na_2CO_3$ aqueous solution was as added thereto. The reaction mixture was reacted at 100° C. for 36 hours.

After the reaction was completed, the reaction mixture was extracted using water and ethyl acetate, and dried. The reaction product was recrystallized using diethyl ether and chloroform to produce the compound (B). The structure of the compound (B) was identified through $^1$H-NMR.

3. Preparation of Compound (C)

Compound (B) (8 g (37.4 mmol)) was dissolved in 100 mL of chloroform, and 15 g (5 equiv.) of bromine was added thereto while the reaction mixture was maintained at 0° C. When the compound (B) vanished completely, addition of bromine was stopped and the reaction mixture was agitated for 10 minutes, followed by adding a trace of acetone to terminate the reaction.

The reaction mixture was extracted using water and $CHCl_3$ to collect the organic layers. The organic layers were dried using $MgSO_4$, concentrated, recrystallized in excess n-hexane to produce the compound (C). The structure of the compound (C) was identified through $^1$H-NMR.

4. Preparation of Compound Represented by Formula 1a

Compound (C) (4 g (10.8 mmol)) and 3.68 g (2.02 eq) of carbazole were dissolved in 70 mL of anhydrous toluene. To this were added 3.1 g (3 eq) of sodium tert-butoxide (NaOtBu), 0.11 g (0.05 eq) of tri(tert-butyl) phosphine ((t-Bu)$_3$P) and 0.4 g (0.04 eq) of Pd$_2$(dba)$_3$ as a catalyst, and reacted at approximately 120° C. for approximately 48 hours.

After the reaction was completed, the reaction product was extracted using water and chloroform, and dried, followed by removing side reaction products through open column chromatography using n-hexane as a development solution, thereby producing the compound represented by formula 1a. The structure of the compound represented by formula 1a was identified through $^1$H-NMR. $^1$H-NMR (CDCl$_3$, δ) 4.01 (s, 6H, 2-OCH$_3$), 7.02–8.24(m, 22H, Aromatic Protons).

PREPARATION EXAMPLE 2

Compound Represented by Formula 1b

Compound (C) (3 g (8.1 mmol)) and 3.57 g (2.02 eq) of N-phenyl-1-naphthylamine were dissolved in 70 mL of anhydrous toluene, and 2.35 g (3 eq) of sodium tert-butoxide (NaOtBu), 0.08 g (0.05 eq) of tri(tert-butyl)phosphine ((t-Bu)$_3$P) and 0.3 g (0.04 eq) of Pd$_2$(dba)$_3$ as a catalyst were added, and reacted at approximately 120° C. for approximately 48 hours.

Figure 3:
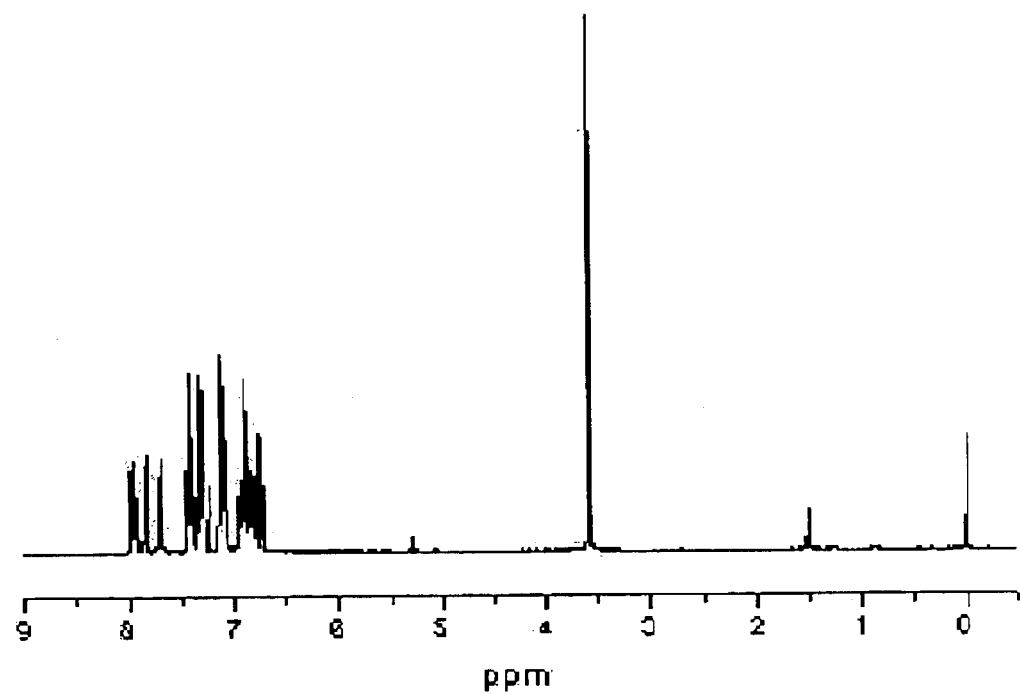
FIG. 3 shows a $^1$H-NMR spectrum of the compound represented by formula 1b according to Synthesis example 2 herein.

After the reaction was completed, the reaction product was extracted using water and ethyl acetate, and dried, followed by removing side reaction products through open column chromatography using n-hexane as a development solution, thereby producing the compound represented by formula 1b. The structure of the compound represented by formula 1b was identified through $^1$H-NMR, as shown in FIG. 3. $^1$H-NMR (CDCl3, δ) 3.59 (s, 6H, 2-OCH3), 6.68–8.03 (m, 3OH, Aromatic Protons).

Figure 4A:
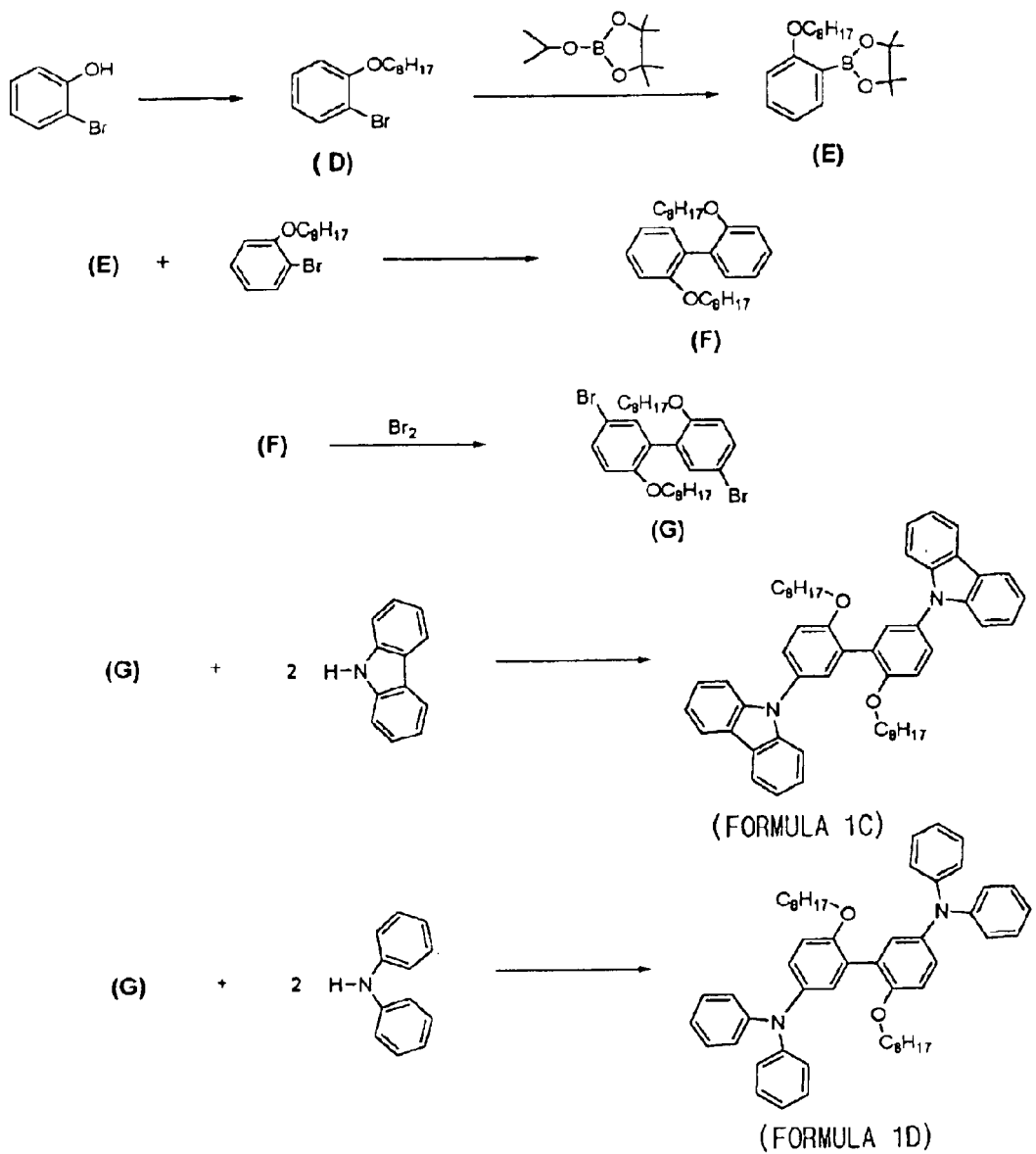
FIG. 4A is a reaction scheme illustrating the synthesis of compounds represented by formulas 1c and 1d according to Synthesis examples 3 and 4 herein.

FIG. 4A schematically shows preparation processes of compounds represented by formulas 1c and 1d, which will now be described in more detail.

PREPARATION EXAMPLE 3

Compound Represented by Formula 1c

1. Preparation of Compound (D)

2-bromophenol (50 g (290 mmol)) was dissolved in 500 mL of acetone and 48.4 g (350 mmol) of $K_2CO_3$ was added thereto. To the reaction product was added 73.3 g (380 mmol) of 1-bromooctane and refluxed for 24 hours.

After the reaction was completed, the reaction mixture was extracted three times using water and $CHCl_3$, followed by removing $K_2CO_3$. Then, organic layers were dried using $MgSO_4$, concentrated, and subjected to column chromatography using n-hexane as a development solution. Unreacted 1-bromooctane was removed from the residue by distillation under reduced pressure, to produce the compound (D). The structure of the compound (D) was identified through $^1$H-NMR.

2. Preparation of Compound (E)

Compound (D) (38 g (130 mmol)) was dissolved in 150 mL of anhydrous THF and cooled to −75° C. and 100 mL (1.2 eq) of n-butyl lithium was slowly added thereto, followed by agitating for about 1 hour. To this was added 32.9 g (1.3 eq) of 2-isopropoxy-4,4,5,5-tetramethyl-1,3,2-dioxaborolane and reacted for 1 hour.

After the reaction was completed, the reaction mixture was extracted three times using water and ethyl acetate, dried using anhydrous $MgSO_4$, and concentrated, followed by subjecting to distillation under reduced pressure to remove unreacted 2-isopropoxy-4,4,5,5-tetramethyl-1,3,2-dioxaborolane to produce the compound (E). The structure of the compound (E) was identified through $^1$H-NMR.

3. Preparation of Compound (F)

Compound (E) (20 g (70 mmol)) and 25 g (1.1 eq) of the compound (D) were dissolved in 100 ml of anhydrous toluene, and 150 mL of 2M $Na_2CO_3$ aqueous solution was added thereto. The reaction mixture was reacted at 100° C. for 36 hours.

After the reaction was completed, the reaction mixture was extracted using water and ethyl acetate, and dried, followed by removing side reaction products through open column chromatography using n-hexane as a development solution, thereby producing the compound (F). The structure of the compound (F) was identified through $^1$H-NMR.

4. Preparation of Compound (G)

Compound (F) (10 g (24.4 mmol)) was dissolved in 150 mL of chloroform, and 8.3 g (2.1 eq) of boron was added thereto while the reaction mixture was maintained at 0° C. After complete removal of the compound (F) from the reaction mixture was confirmed by TLC, addition of bromine was stopped and the reaction mixture was agitated for 10 minutes, followed by adding a trace of acetone to terminate the reaction.

The reaction mixture was extracted using water and $CHCl_3$ to collect the organic layers. The organic layers were dried using $MgSO_4$, concentrated, recrystallized in methanol to produce the compound (G). The structure of the compound (G) was identified through $^1$H-NMR.

5. Preparation of Compound Represented by Formula 1c

Compound (G) (4 g (7.04 mmol)) and 2.38 g (2.02 eq) of carbazole were dissolved in 70 mL of anhydrous toluene, and 2.03 g (3 eq) of sodium tert-butoxide (NaOtBu), 0.07 g (0.05 eq) of tri(tert-butyl)phosphine ((t-Bu)$_3$P) and 0.26 g (0.04 eq) of Pd$_2$(dba)$_3$ as a catalyst were added, and reacted at approximately 120° C. for approximately 48 hours.

After the reaction was completed, the reaction product was extracted using water and ethyl acetate, and dried, followed by removing side reaction products through open column chromatography using n-hexane as a development solution, thereby producing the compound represented by formula 1c. The structure of the compound represented by formula 1c was identified through $^1$H-NMR. $^1$H-NMR (CDCl$_3$, δ) 0.72–1.81 [m, 30H, 2-(CH$_2$)$_6$CH$_3$], 4.01 (t, 4H, 2-OCH$_2$—), 2.02–8.24 (m, 22H, Aromatic Protons).

Figure 4B:
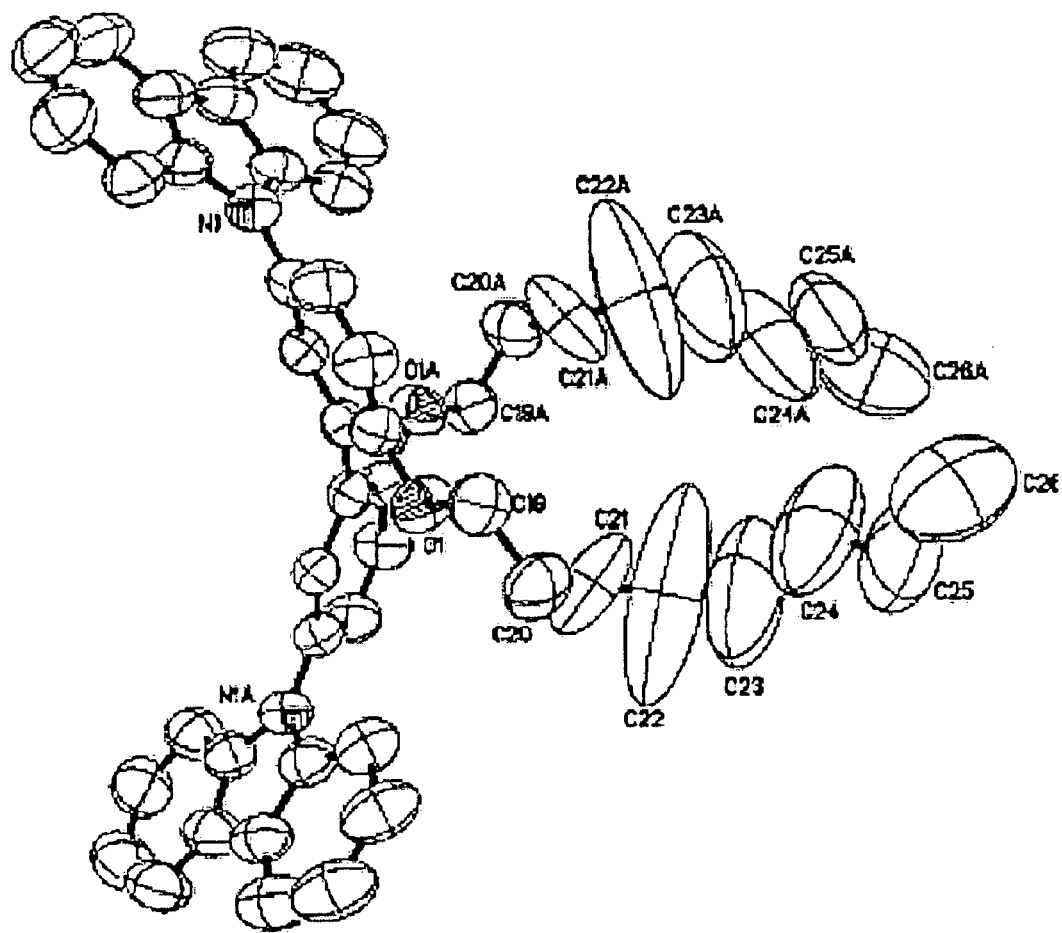
FIG. 4B illustrates an X-ray crystal structure of a compound represented by formula 1c according to Synthesis example 3 herein.

FIG. 4B shows an X-ray crystal structure of the compound represented by formula 1c according to Synthesis Example 3 of the present invention.

PREPARATION EXAMPLE 4

Compound Represented by Formula 1d

Compound (G) (4 g (7.04 mmol)) and 2.41 g (2.02 eq) of diphenylamine were dissolved in 70 mL of anhydrous toluene, and 2.03 g (3 eq) of sodium tert-butoxide (NaOtBu), 0.07 g (0.05 eq) of tri(tert-butyl)phosphine ((t-Bu)$_3$P) and 0.26 g (0.04 eq) of Pd$_2$(dba)$_3$ as a catalyst, and reacted at approximately 120° C. for approximately 48 hours.

Figure 5:
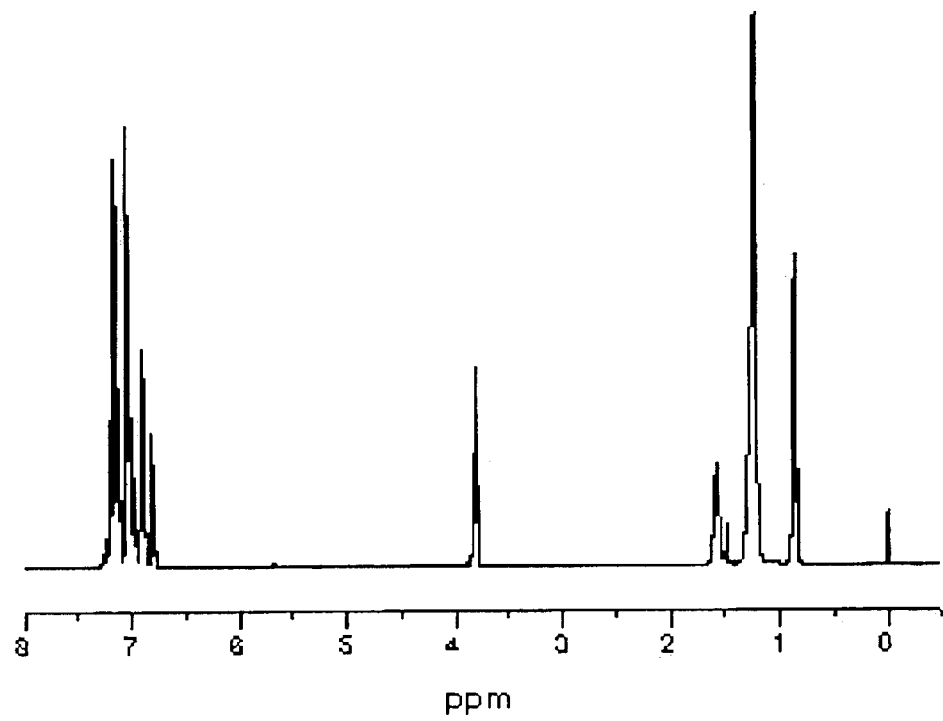
FIG. 5 illustrates a $^1$H-NMR spectrum of a compound represented by formula 1d according to Synthesis example 4 herein.

After the reaction was completed, the reaction product was extracted using water and ethyl acetate, and dried, followed by removing side reaction products through open column chromatography using n-hexane as a development solution, thereby producing the compound represented by formula 1d. The structure of the compound represented by formula 1c was identified through $^1$H-NMR, as shown in FIG. 5. $^1$H-NMR (CDCl$_3$, δ) 0.71–1.79 (m, 30H, 2-(CH$_2$)$_6$CH$_3$), 3.83 (t, 4H, 2-OCH$_2$—), 6.81–7.3 (m, 26H, Aromatic Protons).

Figure 6:
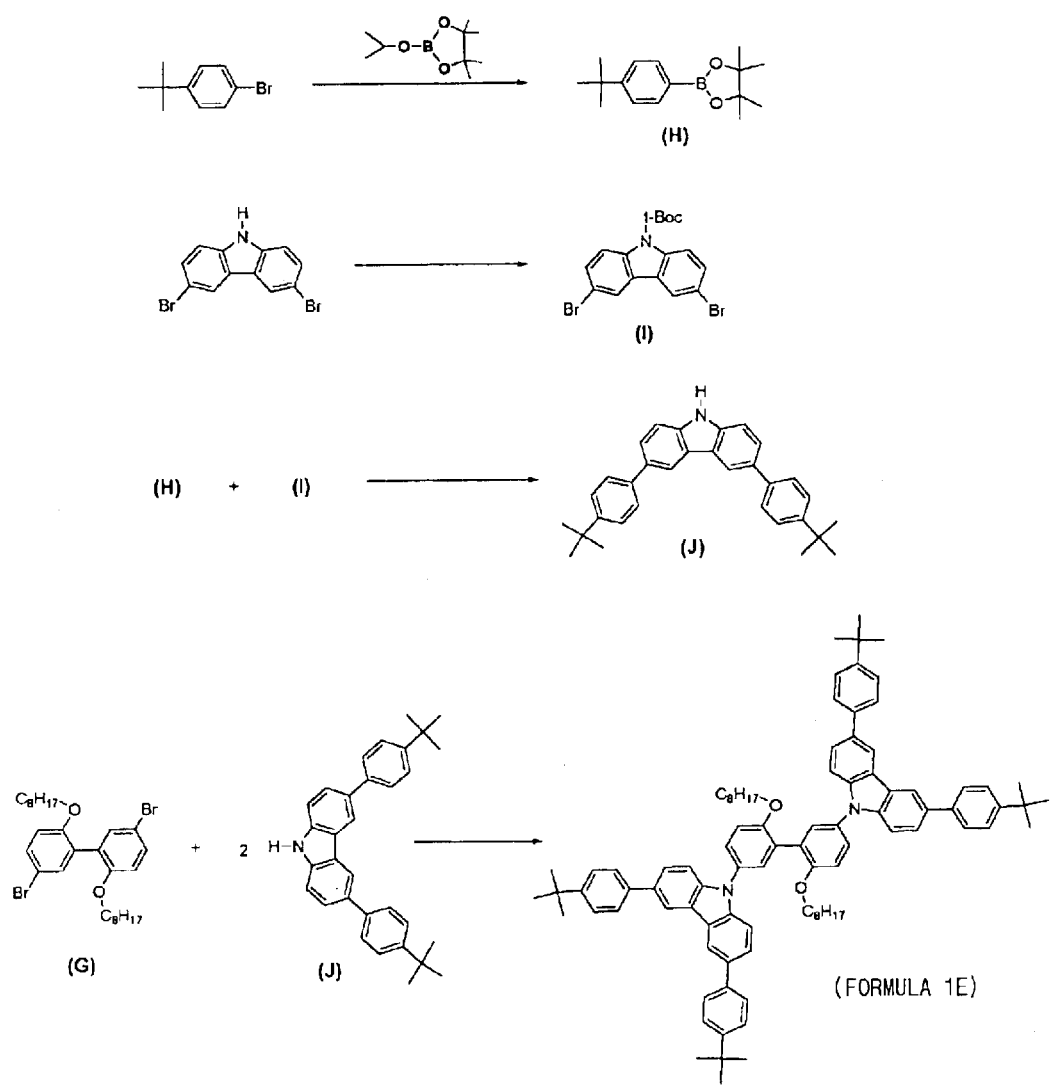
FIG. 6 is a reaction scheme illustrating the synthesis of a compound represented by formula e according to Synthesis example 5 herein.
Figure 7:
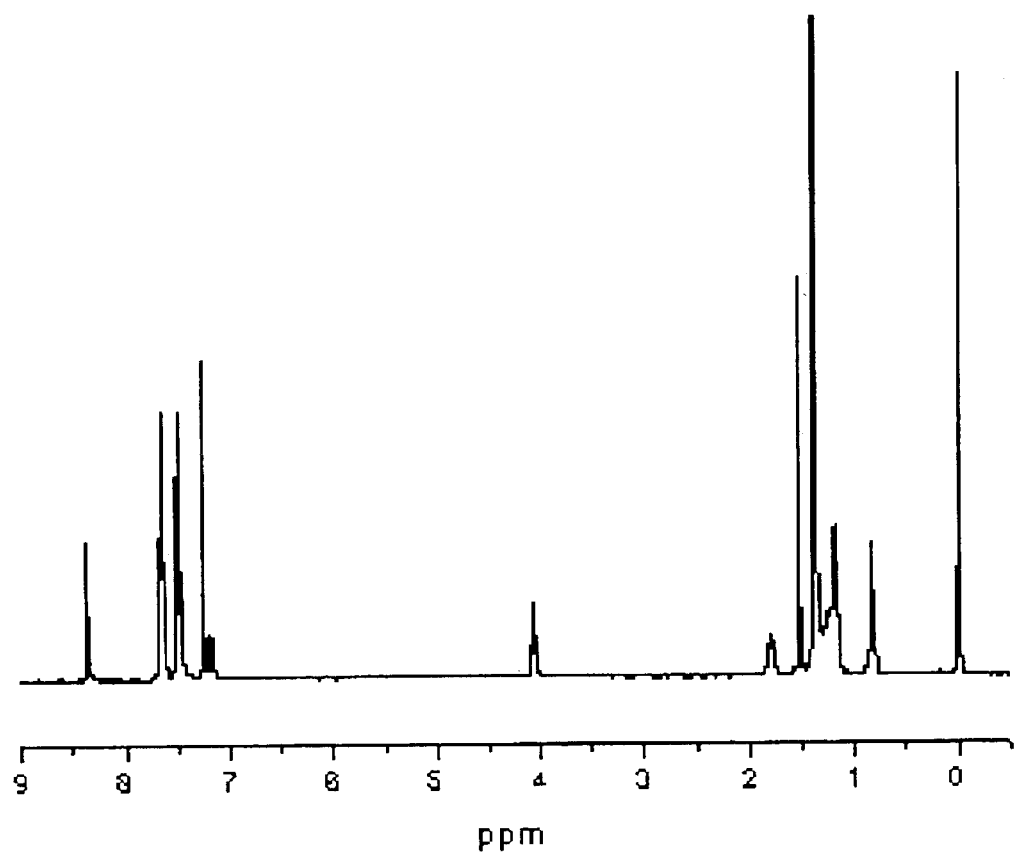
FIG. 7 illustrates a $^1$H-NMR spectrum of a compound represented by formula 1e according to Synthesis example 5 herein.

FIG. 6 is a reaction scheme illustrating the synthesis of a compound represented by formula 1e according to Synthesis Example 5 of the present invention.

PREPARATION EXAMPLE 5

Compound Represented by Formula 1e

1. Preparation of Compound (H)

1-bromo-4-tert-butylbenzene (47.5 g (0.223 mol)) was dissolved in 500 mL of anhydrous THF and cooled to –70° C., and 127.4 mL (0.3185 mol) of 2.5M n-butyl lithium was slowly added thereto, followed by agitating for about 30 minutes. To this was added 50 mL (0.245 mol) of 2-isopropoxy-4,4,5,5-tetramethyl-1,3,2-dioxaborolane and agitated for about 1 hour.

After the reaction was completed, 500 mL of distilled water was added to the reaction mixture, forming white precipitate. The precipitate was filtered, washed with 200 mL of distilled water, and dried under reduced pressure, to produce 43 g of the compound (H). The structure of the compound (H) was identified through $^1$H-NMR.

2. Preparation of Compound (I)

9-H-3,3-bromocarbazole (70 g (0.22 mol)) was dissolved in 1 L of THF. To this were added 56.7 g (0.26 mol) of (Boc)$_2$O, where Boc represents a tert-butoxycarbonyl group, and 3.2 g (0.026 mol) of 4-dimethylaminopyridine (DMAP), and agitated at room temperature for approximately 12 hours.

After the reaction was completed, the reaction mixture was concentrated under reduced pressure, and 1 L of ethyl acetate and 1 L of water were added thereto to separate organic layers. The organic layers were washed with 1 L of 1N HCl aqueous solution, 1 L of water and 1 L of NaHCO$_3$ aqueous solution and dried under reduced pressure, to produce the compound (I) as a white solid. The structure of the compound (I) was identified through $^1$H-NMR.

3. Preparation of Compound (J)

Compound (H) (49 g (0.188 mol)) and 24 g (0.055 mol) of the compound (I) were added to 300 mL of toluene and 200 mL of distilled water, and 1.2 g (5.5 mol) of Pd(OAc)$_2$ and 53 g of K$_2$CO$_3$ were added thereto, followed by agitating at approximately 70° C. for approximately 16 hours.

After the reaction was completed, the reaction product was extracted using 400 mL of ethyl acetate and concentrated under reduced pressure.

Trifluoroacetic acid (TFA-30 mL) and 100 mL of dimethyl formamide (DMF) were added to the residue produced after the distillation, and agitated at approximately 100° C. for approximately 48 hours. Thereafter, the resultant product was concentrated under reduced pressure to remove TFA, and 100 mL of a 2N NaOH solution and 100 mL of water were added thereto, giving a white solid compound. The obtained compound was filtered and washed with 100 mL of ethyl acetate, to produce 20 g of the compound (J). The structure of the compound (J) was identified through $^1$H-NMR. $^1$H-NMR (DMSO-d$_6$, δ) 1.33 (m, 18 H, 2-C(CH$_3$)$_3$), 3.91 (t, 4H, 2-OCH$_2$—), 7.20–8.75 (m, 14H, Aromatic Protons), 11.3 (s, 1H, —N—H of carbazole).

4. Preparation of Compound Represented by Formula 1e

Compound (G) (1.2 g (2.1 mmol)) and 1.87 g (2.05 eq) of the compound (D) were dissolved in 40 mL of anhydrous toluene. To this were added 0.61 g (3 eq) of sodium tert-butoxide (NaOtBu), 0.02 g (0.05 eq) of tri(tert-butyl) phosphine ((t-Bu)$_3$P) and 0.084 g (0.04 eq) of Pd$_2$(dba)$_3$ as a catalyst, and reacted at approximately 120° C. for approximately 48 hours.

After the reaction was completed, the reaction product was extracted using water and chloroform, and dried, followed by removing side reaction products through open column chromatography using n-hexane as a development solution, thereby producing the compound represented by formula 1e. The structure of the compound represented by formula 1e was identified through $^1$H-NMR. $^1$H-NMR (CDCl$_3$, δ) 0.72–1.89 [m, 48H, 2-(CH$_2$)$_6$CH$_3$ & 2-C(CH$_3$)$_3$] 4.07 (t, 4H, 2-OCH$_2$—), 7.10–8.44 (m, 34H, Aromatic Protons).

Optical properties of the compounds represented by formula 1a, 1c and 1d prepared in Preparation Examples were evaluated. The optical properties were evaluated by dissolving the compounds in chlorobenzene and measuring UV-VIS spectra and PL (photoluminescence) spectra of the compounds.

Figure 8:
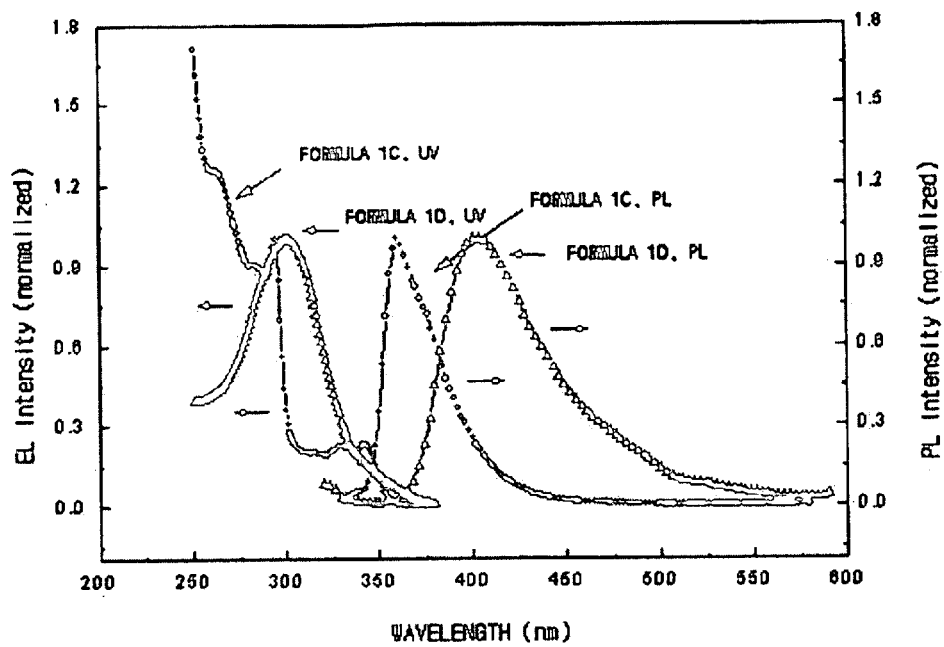
FIG. 8 illustrates UV-VIS absorption spectra and PL (photoluminescent) spectra of compounds represented by formulas 1c and 1d according to Synthesis examples 3 and 4 herein.

The measurement results are shown in FIG. 8. Referring to FIG. 8, the UV-VIS absorption spectrum illustrated that the compound represented by formula 1c exhibited three characteristic peaks, that is, 291 nm, 329 nm and 342 nm. The maximum PL peak measured using the excitation wavelength of 291 nm was approximately 360 nm. Although not shown in FIG. 8, the optical property of the compound represented by formula 1a is substantially the same as that of the compound represented by formula 1c. The compound represented by formula 1d exhibited a UV absorption peak of 301 nm. The maximum PL peak measured using the excitation wavelength of 301 nm was approximately 401 nm.

Optical properties of the compound represented by formula 1e prepared in Preparation Example 5 and states of a thin film formed of the same were evaluated. The thin film was formed by dissolving the compound represented by formula 1e in chlorobenzene, spin-coating the same on a quartz substrate and drying. The states of the formed thin film were observed by a polarizing microscope, and the optical properties of the compound were evaluated by dissolving the same in chlorobenzene and measuring UV-VIS spectra and PL (photoluminescence) spectra of the compound.

Figure 9:
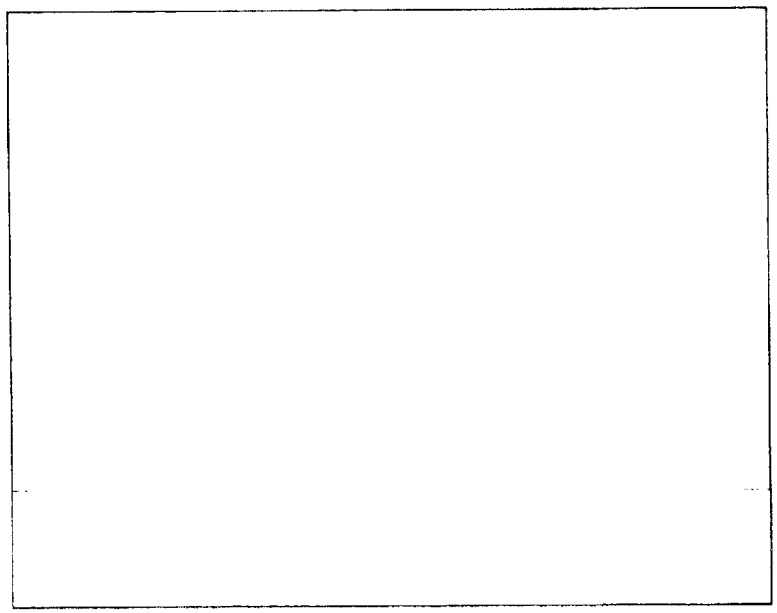
FIG. 9 illustrates a polarizing microscope photograph of a thin film containing a compound represented by formula 1e according to Synthesis example 5 herein.

FIG. 9 shows a polarizing microscope photograph of the thin film containing the compound represented by formula 1e according to Synthesis Example 5 of the present invention. As shown in FIG. 9, the film is at a homogenous state without defects, such as pin holes, and has no crystalline domain.

Figure 10:
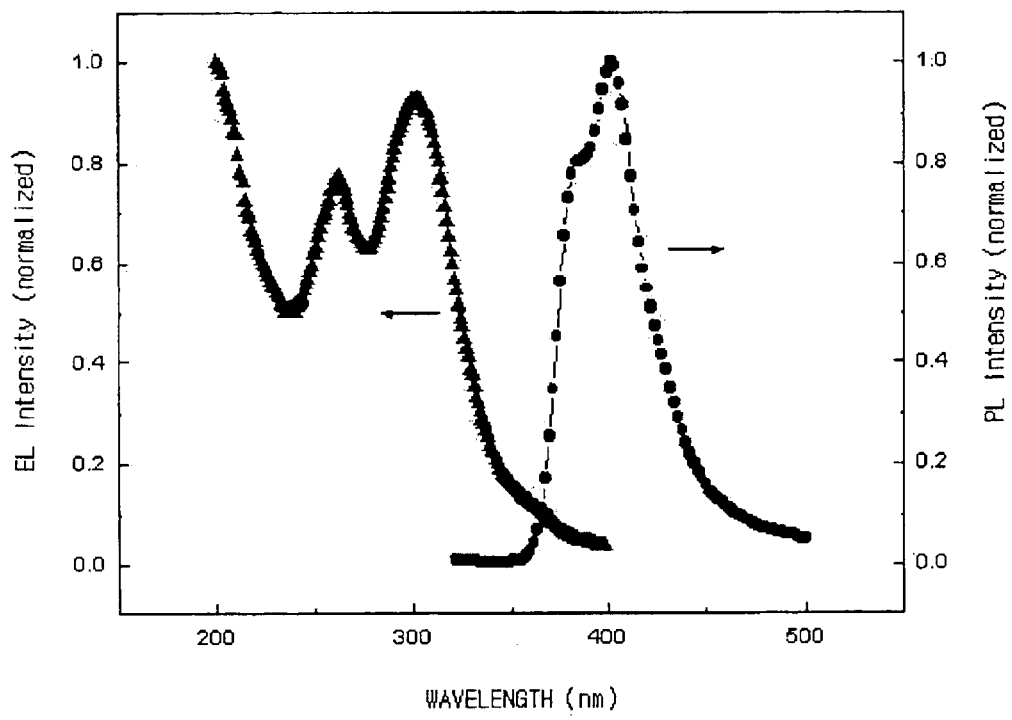
FIG. 10 illustrates UV-VIS absorption spectrum and PL (photoluminescent) spectrum of a thin film made of a compound represented by formula 1e according to Synthesis example 5 herein.

FIG. 10 shows UV-VIS absorption spectrum and PL (photoluminescent) spectrum of the thin film made of the compound represented by formula 1e according to Synthesis Example 5 of the present invention. Referring to FIG. 10, the compound represented by formula 1e exhibited UV absorption peaks at 262 nm and 302 nm. The maximum PL peak measured using the excitation wavelength of 302 nm was approximately 402 nm.

To examine energy transfer characteristics, HOMO and LUMO energy levels of the compound represented by formula 1e, when used as a phosphorescent host material, were measured. The measured energy levels are shown in FIG. 11A, and PL spectrum and UV-VIS absorption spectrum of the compound represented by formula 1e are shown in FIG. 11B and FIG. 12, respectively.

Figure 11A:
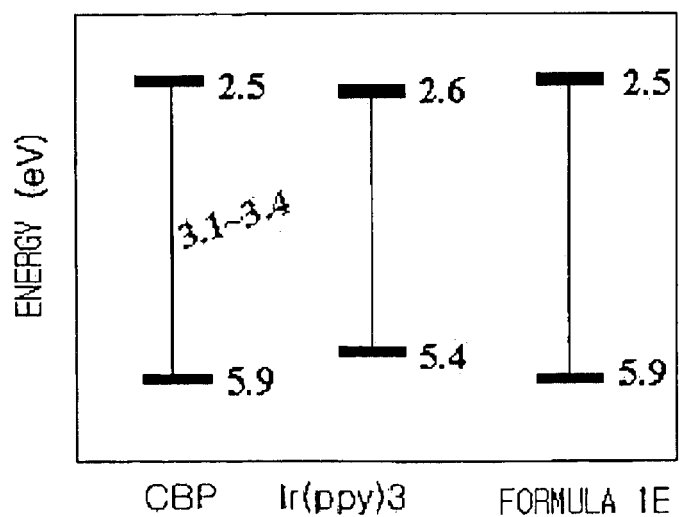
FIG. 11A shows band gaps of a metal complex (Ir(ppy)$_3$) and the compound represented by formula 1e according to Synthesis Example 5 of the present invention.
Figure 11B:
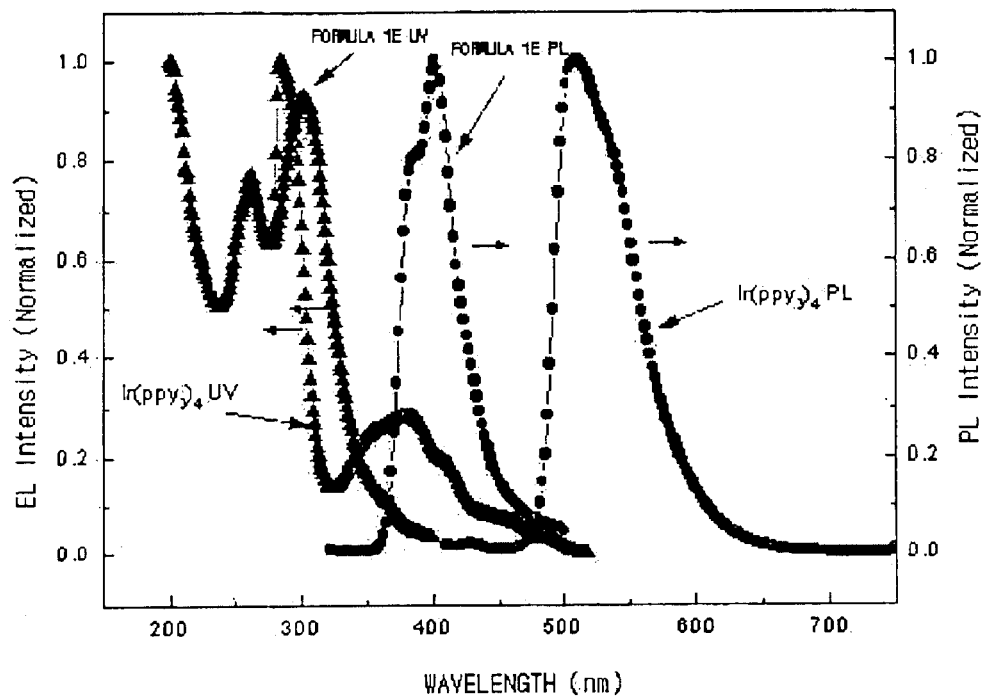
FIG. 11B shows UV-VIS absorption spectrum and PL (photoluminescent) spectrum of the compound represented by formula 1e according to Synthesis Example 5 of the present invention.
Figure 12:
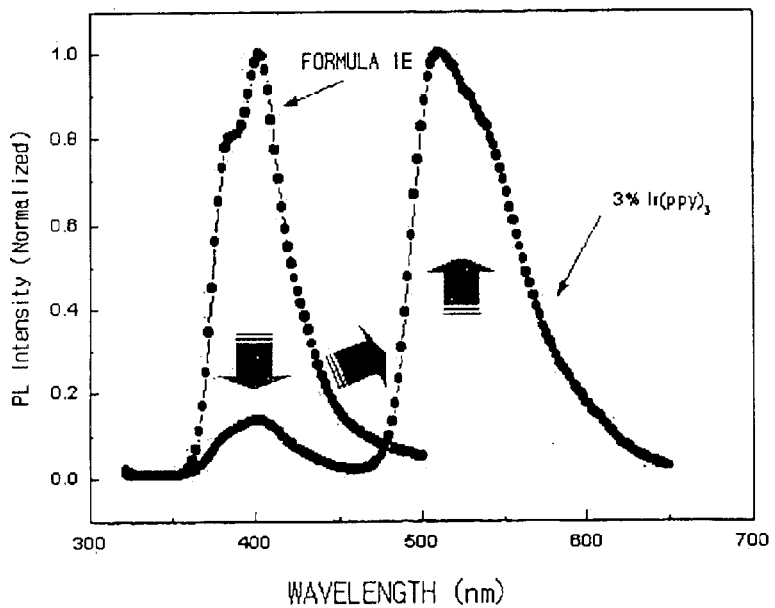
FIG. 12 shows UV-VIS absorption spectra and PL (photoluminescent) spectra of a thin film containing the metal complex (Ir(ppy)$_3$) and a thin film containing the compound represented by formula 1e according to Synthesis Example 5 of the present invention.

FIG. 11A also shows HOMO and LUMO energy levels of 4,4'-N,N'-dicarbazole-biphenyl (CBP), which is a representative phosphorescent host material, and metal complex (Ir(ppy)$_3$) as a dopant, for reference.

Band gaps of the metal complex and the host material are believed to be important criteria to manufacture a highly efficient EL device, since excited excitons in the host material should be effectively transferred to the metal complex. A compound covering an energy range between the HOMO and LUMO energy levels of a metal complex and having a band gap lower than that of the metal complex, is preferably used as the phosphorescent host material. Also, since it is known that as PL spectral emission of a host material overlaps UV-VIS absorption spectral emission of a metal complex as much as possible, the emission efficiency is higher, materials satisfying such requirements are preferably used as the phosphorescent host material. Representative examples of suitable phosphorescent materials meeting such requirements include a mixed material of CBP as a host and Ir(ppy)$_3$ as an iridium metal complex.

Referring to FIG. 11A, the band gap of CBP ranges from about 3.1 to about 3.4 ev, the band gap of iridium metal complex ranges from about 2.6 to about 2.8 ev. That is, the HOMO-LUMO energy range of iridium metal complex falls within that of CBP. In addition, the compound represented by formula 1e has substantially the same band gap with CBP. Referring to FIG. 11B, it was observed that the PL spectral emission of the compound represented by formula 1e almost coincided with the UV-VIS absorption spectral emission of Ir(ppy)$_3$.

FIG. 12 shows PL spectra of a thin film comprising 97% by weight of the compound represented by formula 1e and 3% by weight of the metal complex (Ir(ppy)$_3$) and a thin film comprising the compound represented by formula 1e. The thin film formed of the compound represented by formula 1e exhibits the maximum PL peak at about 402 nm. In the thin film comprising 97% by weight of the compound represented by formula 1e and 3% by weight of the metal complex (Ir(ppy)$_3$), the maximum PL peak was shifted to 510 nm, which is a characteristic peak of Ir(ppy)$_3$. This is believed to be due to the excitation energy of the compound represented by formula 1e being transferred to the metal complex, which in turn produces photoluminescence. Therefore, although the compound represented by formula 1e has a low molecular weight, it can form a thin film by spin coating and can be advantageously used as a phosphorescent host material that is compatible with a metal complex in view of energy transfer.

Thermal properties of the compounds represented by formulas 1a–1e prepared in the above-described preparation examples were examined by TGA (Thermogravimetric analysis) and DSC (Differential Scanning Calorimetry). The thermal properties were measured under nitrogen atmosphere at a speed of 10° C./min.

Figure 13:
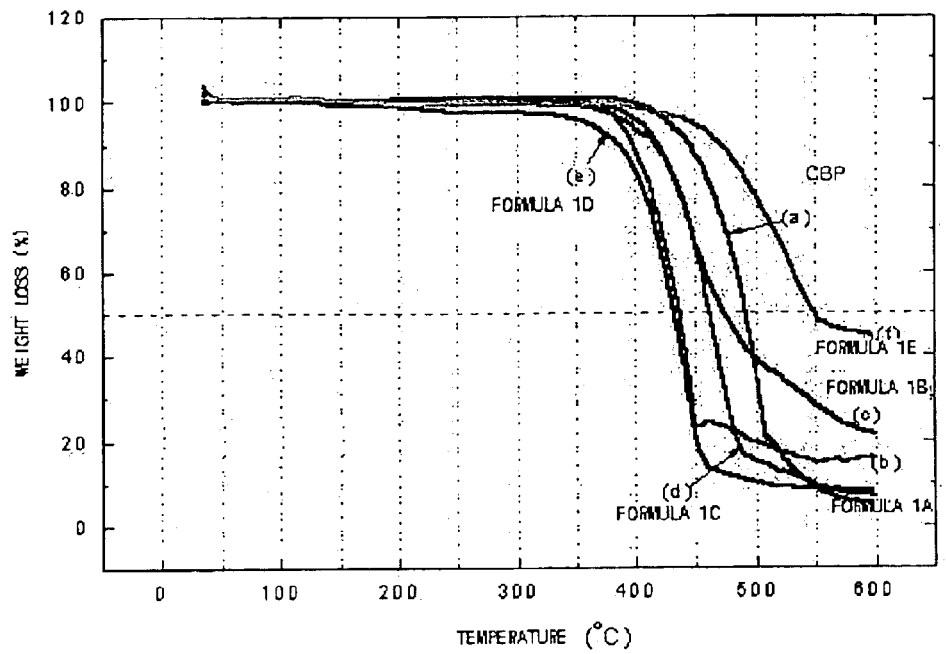
FIG. 13 is a thermogravimetric analysis (TGA) graph of compounds represented by formulas 1a–1e according to Synthesis examples 1–5 herein and CBP.

The results of TGA examination are shown in FIG. 13. CBP as the conventional phosphorescent host material experienced a sharp loss in weight at approximately 400° C., while the compounds represented by formulas 1a–1d showed a loss in weight at a lower temperature than 400° C., which is presumably due to alkyl substituent in the biphenyl backbone.

However, although the compound represented by formula 1e has a long chain alkyl substituent in the biphenyl backbone, it began to lose its weight at approximately 450° C., which is higher than in the case of CBP. A temperature at which approximately 50% by weight of the compound represented by formula 1e remained, was approximately 550° C., which is also higher than in the case of CBP. This suggests that thermal stability of the compound represented by formula 1e is higher than that of CBP.

Figure 14A:
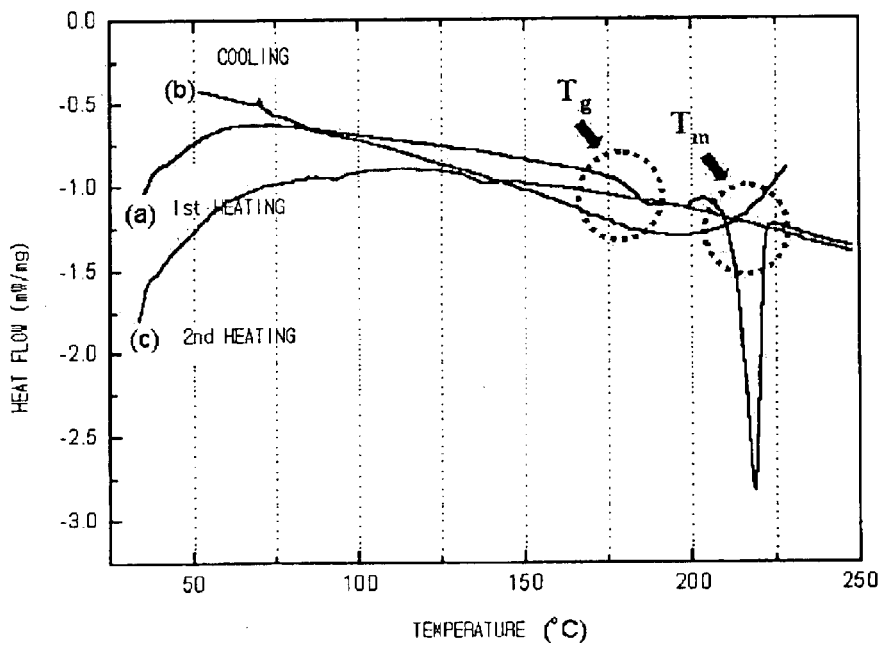
FIG. 14A is a differential scanning calorimeter (DSC) graph of a compound represented by formula 1e according to Synthesis example 5 herein.
Figure 14B:
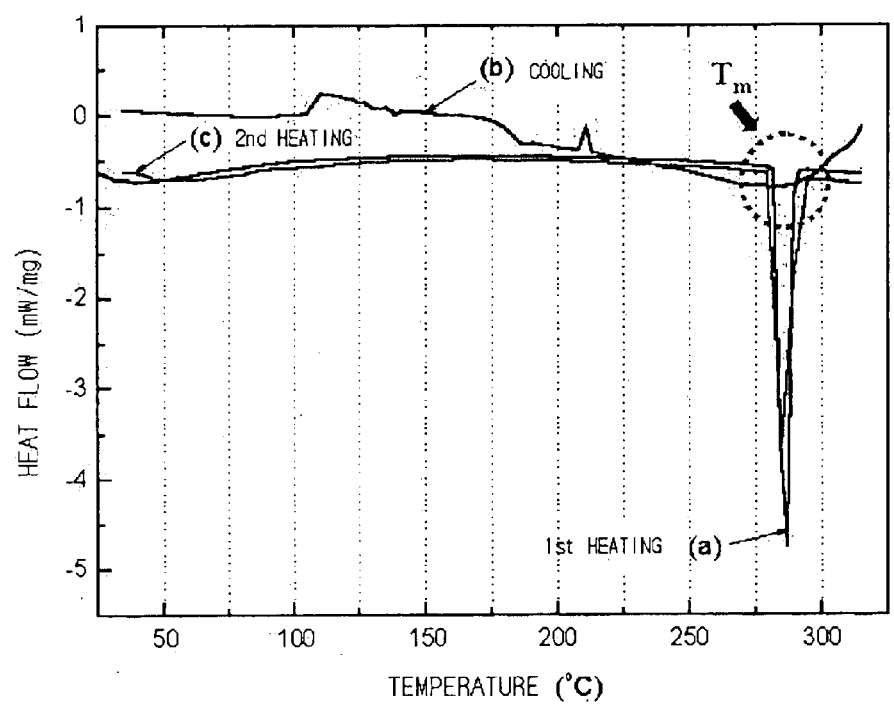
FIG. 14B is a DSC graph of CBP.

The results of DSC examination are shown in FIGS. 14A and 14B. A glass transition temperature (Tg) of the compound represented by formula 1e was observed at approximately 170° C., and a melting point thereof was not distinct, unlike most low molecular weight EL materials. The compound represented by formula 1e was neither recrystallized nor melted in the course of recooling and reheating once melted at approximately 220° C., which also is applied to the compounds represented by formulas 1a–1d. This is presumably because the compounds represented by formulas 1a–1e became completely amorphous once melted due to severe steric hindrance during crystallization, arising from a twisted biphenyl aromatic ring structure contained in the compounds represented by formulas 1a–1e, particularly, a bulky substituent contained in the compound represented by formula 1e.

Therefore, since the compounds represented by formulas 1a–1e, particularly, the compound represented by formula 1e, have high crystal stability as well as high thermal stability, they can be used advantageously as the host material for an EL device employing a phosphorescent material.

EXAMPLE 1

Manufacture of Organic EL Device

A transparent electrode layer coated with indium-tin oxide (ITO) was cleaned. The ITO layer was patterned into a desired shape using a photoresist resin and etchant to form an ITO electrode pattern, and washed. Poly(styrene sulfonate)-doped poly(3,4-ethylenedioxy thiophene) (PEDOT) (available from Bayer Co. under the trade name of BATRON® P 4083) was coated on the patterned ITO layer to a thickness of 500 Å and baked at 180° C. for about 1 hour to form a hole injection layer.

A mixture of the compound represented by formula 1e prepared in Preparation Example 5 and 6.6% by weight of Ir(ppy)$_3$ was dissolved in 1.5% by weight of chlorobenzene to obtain an EL layer composition. The EL layer composition was spin coated on the hole injection layer, baked at 90° C. for 2 hours, and placed in a vacuum oven to fully remove the solvent, forming an emissive layer to a thickness of approximately 800 Å.

Next, Balq was vacuum deposited on the emissive layer in a vacuum deposition chamber at a vacuum of 4×10$^{-6}$ torr to form a hole blocking layer having a thickness of 100 Å. Subsequently, Alq3 was vacuum deposited on the hole blocking layer to form an electron transport layer having a thickness of approximately 200 Å, and LiF was vacuum deposited thereon at a deposition rate of 0.1 Å/sec to form an electron injection layer having a thickness of 10 Å. Then, aluminum (Al) was vacuum deposited on the resultant structure at a deposition rate of 0.1 Å/sec to form an anode having a thickness of approximately 2000 Å, followed by encapsulating, thereby manufacturing an organic EL device. Here, the device was encapsulated in a glove box maintained at a dry nitrogen atmosphere such that BaO powder was placed in a metal can and hermetically sealed, and finally subjected to treatment with a UV curing agent.

Figure 15:
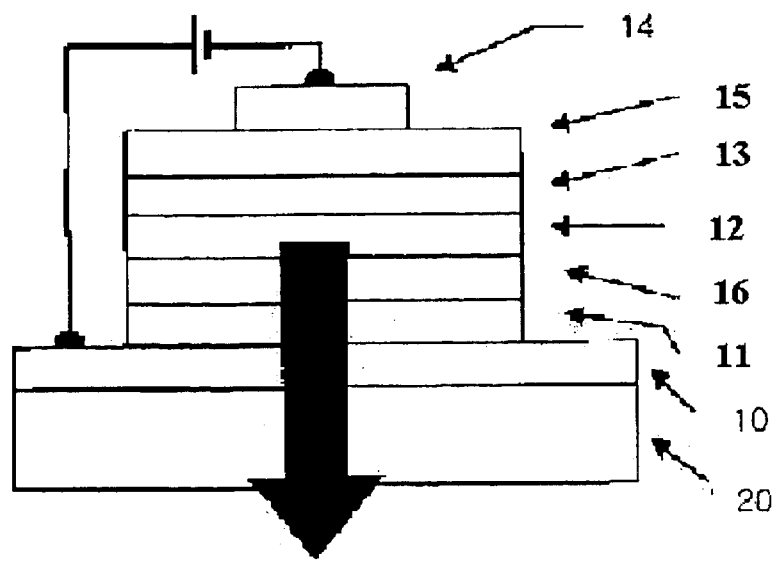
FIG. 15 shows a cross-section of an organic EL device manufactured in example 1 herein.

The resulting EL device had a multiple-layered structure, as illustrated in FIG. 15. The emissive area was approximately 6 mm$^2$.

EXAMPLES 2–5

Manufacture of Organic ELs

Organic EL devices were manufactured in the same manner as in Example 1, except that the compounds represented by formulas 1a–1d were used instead of the compound represented by formula 1e, to prepare emissive layers.

Figure 16:
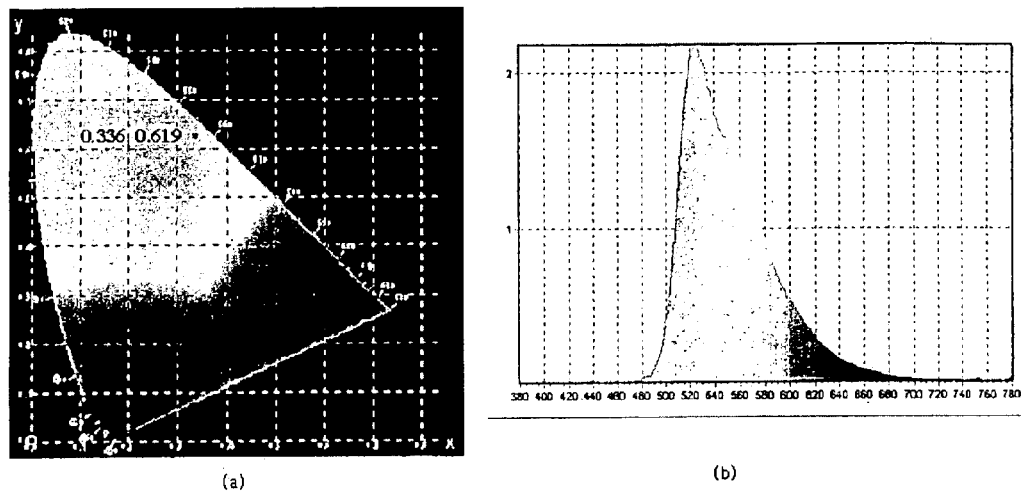
FIG. 16A shows color coordinate characteristics of the organic EL device manufactured in example 1 herein.
FIG. 16B illustrates an EL spectrum of an organic EL device manufactured in example 1 herein.
Figure 17:
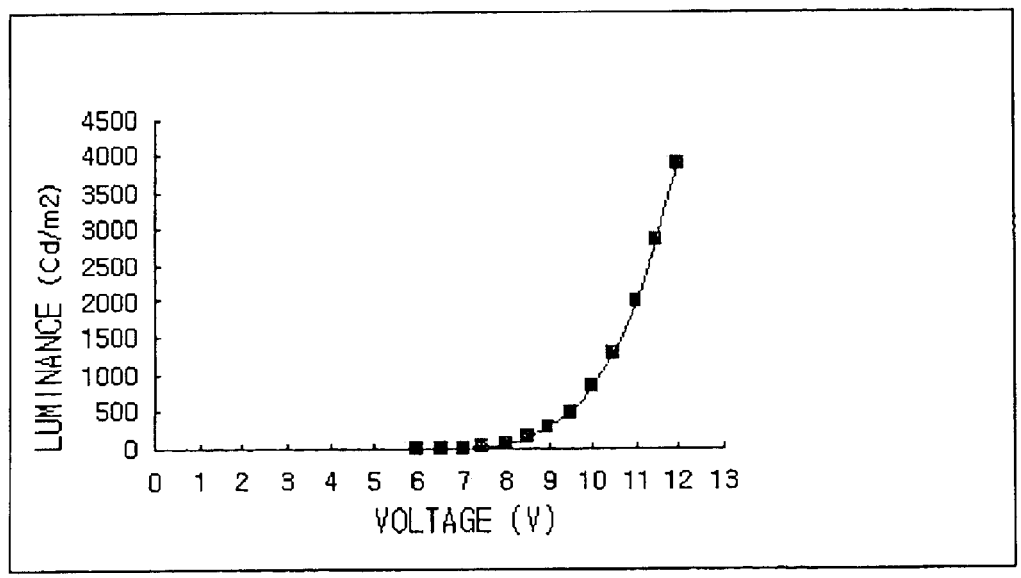
FIG. 17 is a graph of luminance versus voltage for an organic EL device manufactured in example 1 herein.
Figure 18:
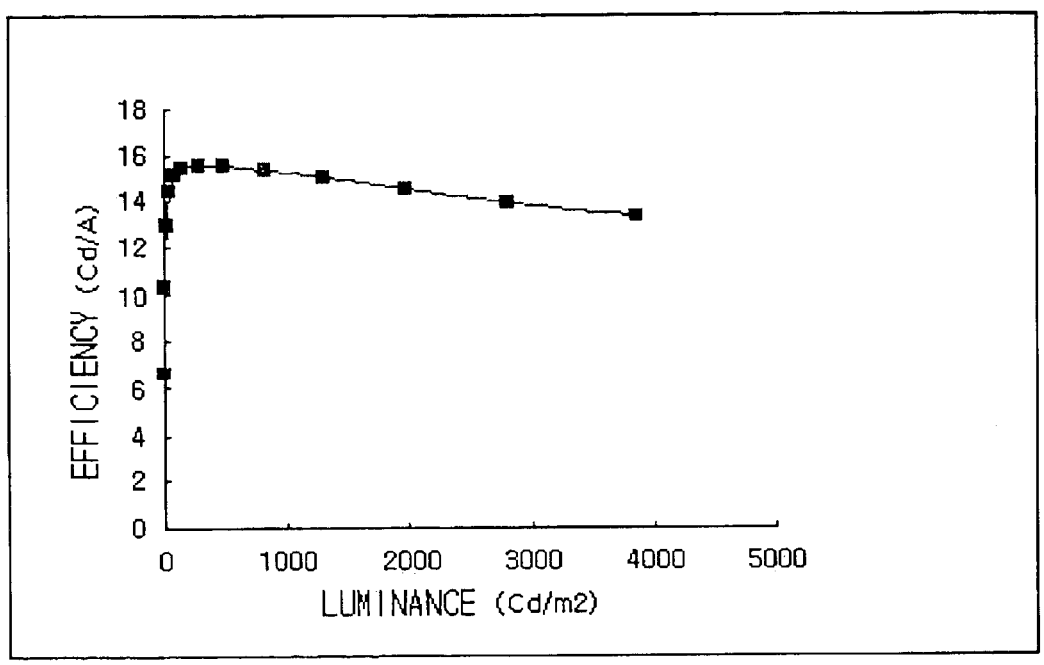
FIG. 18 is a graph of luminance versus EL efficiency (cd/A) for an organic EL device manufactured in example 1 herein.

The color coordinate properties and EL properties of the organic EL device of Example 1 were evaluated, and the results are shown in FIGS. 16–18. For evaluation of EL properties, a forward bias voltage was applied as a direct current (DC) driving voltage.

FIG. 16A shows color coordinate characteristics of the organic EL device manufactured in Example 1 of the present invention. Referring to FIG. 16A, light emission was initiated from the metal complex Ir(ppy)$_3$ in the emissive layer and had 1931 CIE color coordinates (0.34, 0.62) at 800 cd/m$^2$ The EL spectrum of the organic EL device manufactured in Example 1 of the present invention, as shown in FIG. 16B, corresponds to a green color emission. This suggests that the exciton excited from the compound represented by formula 1e was transferred to the metal complex, thus producing light. Also, The manufactured organic EL device exhibited uniform surface emission and typical rectifying diode's characteristics.

FIG. 17 is a graph of luminance versus voltage for the organic EL device manufactured in Example 1 of the present invention, and FIG. 18 is a graph of luminance versus EL efficiency (cd/A) for the organic EL device manufactured in Example 1 according to the present invention.

Referring to FIG. 17, a driving voltage of the organic EL device manufactured in Example 1 of the present invention was approximately 6 V. The maximum luminance of the organic EL device manufactured in Example 1 of the present invention was approximately 15.5 cd/A. Also, the organic EL devices manufactured in Examples 2–5 exhibited substantially the same color coordinate and EL characteristics with those of the organic EL device manufactured in Example 1.

As described above, according to the present invention, an organic EL device employing in its emissive layer a phosphorescent host compound having a biphenyl derivative in its backbone and having an amino group substituted or unsubstituted with an alkoxy group introduced to the biphenyl derivative, can be manufactured. Thus, disadvantages associated with the use of conventional low molecular weight/polymer host materials are not necessarily realized with preferred embodiments of the present invention. In addition, an organic EL device with high thermal, crystal stability, improved formability and high emission efficiency can be manufactured.

The invention has been described with particular reference to preferred embodiments and examples. Those skilled in the art will appreciate that the invention is not limited to those preferred embodiments and that various modifications are within the scope of the invention. Moreover, the description herein of disadvantages associated with known materials, methods, and apparatus is not intended to limit the invention. Indeed, certain aspects of the invention may include one or more known materials, methods, and apparatus without suffering from the disadvantages.

What is claimed is:

1. A biphenyl derivative represented by formula 1:

<Formula 1>

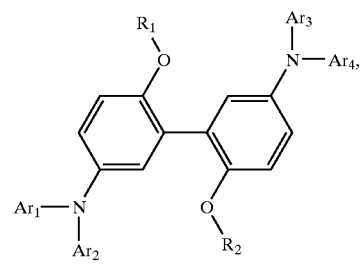

wherein:

$R_1$ and $R_2$ are independently a hydrogen; a $C_{1-20}$ linear or branched alkyl group; a $C_{5-20}$ cycloalkyl group; a $C_{6-20}$ aryl group; and a $C_{6-20}$ aryl group having at least one substituent selected from the group consisting of a halogen atom, a $C_{1-10}$ halogenated alkyl group, —Si(R)(R')(R"), a $C_{1-10}$ alkyl group, a $C_{1-10}$ alkoxy group, a $C_{6-10}$ aryl group, a $C_{4-10}$ heteroaryl group, and —N(R)(R');

$Ar_1$, $Ar_2$, $Ar_3$ and $Ar_4$ are independently a hydrogen; a $C_{1-20}$ linear or branched alkyl group; a $C_{5-20}$ cycloalkyl group; a $C_{6-20}$ aryl group; and a $C_{6-20}$ aryl group having at least one substituent selected from the group consisting of a halogen atom, a $C_{1-10}$ halogenated alkyl group, —Si(R)(R')(R"), a $C_{1-10}$ alkyl group, a C-$_{1-10}$ alkoxy group, a $C_{6-10}$ aryl group, a $C_{4-10}$ heteroaryl group and —N(R)(R') or at least one selected from the group consisting of $Ar_1$ and $Ar_2$, and $Ar_3$ and $Ar_4$ are joined together to form a fused ring structure with the N to which they are attached; and R, R' and R" are independently selected from the group consisting of a hydrogen atom, a $C_{1-10}$ alkyl group, a $C_{1-10}$ alkoxy group, a $C_{6-10}$ aryl group and a $C_{4-10}$ heteroaryl group.

2. The biphenyl derivative of claim 1, wherein in formula 1, —N(Ar$_1$)(Ar$_2$) and/or —N(Ar$_3$)(Ar$_4$) are independently a group represented by formula 2:

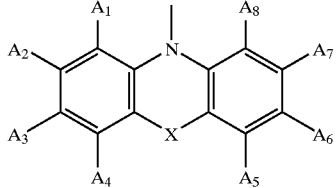

<Formula 2> wherein:

X is a single bond or —(CH$_2$)$_n$—, where n is an integer of 1~2, —C(R$_3$)(R$_4$)—, —CH=CH—, —S—, —O— or —Si(R$_3$)(R$_4$)—;

A$_1$, A$_2$, A$_3$, A$_4$, A$_5$, A$_6$, A$_7$, A$_8$, R$_3$, and R$_4$, are independently a hydrogen atom; a C$_{1-20}$ linear or branched alkyl group; a C$_{5-20}$ cycloalkyl group; a C$_{5-20}$ aryl group; and a C$_{5-20}$ aryl group having at least one substituent selected from the group consisting of a halogen atom, a C$_{1-10}$ halogenated alkyl group, —Si(R)(R')(R"), a C$_{1-10}$ alkyl group, a C$_{1-10}$ alkoxy group, a C$_{6-10}$ aryl group, a C$_{4-10}$ heteroaryl group and —N(R)(R'), at least one selected from the group consisting of A$_1$ and A$_2$, A$_2$ and A$_3$, A$_3$ and A$_4$, A$_5$ and A$_6$, A$_6$ and A$_7$, and A$_7$ and A$_8$ being interconnected, respectively; and R, R' and R" are independently selected from the group consisting of a hydrogen, a C$_{1-10}$ alkyl group, a C$_{1-10}$ alkoxy group, a C$_{6-10}$ aryl group and a C$_{4-10}$ heteroaryl group.

3. The biphenyl derivative of claim 2, wherein the group represented by formula (2) is one selected from the group consisting of groups (2a) through (2h):

(2a)
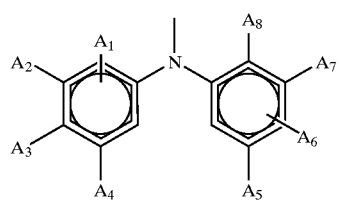

(2b)
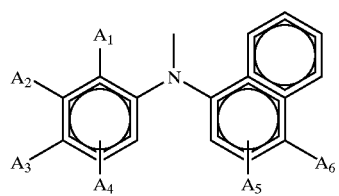

(2c)
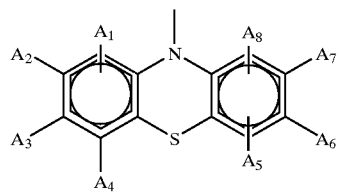

(2d)
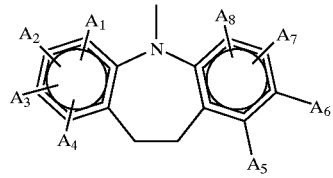

(2e)
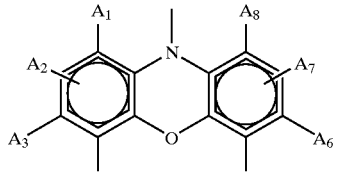

(2f)
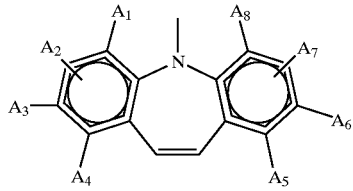

(2g)
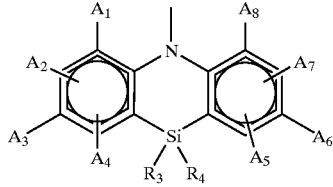

(2h)
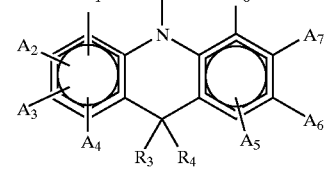

wherein:

A$_1$, A$_2$, A$_3$, A$_4$, A$_5$, A$_6$, A$_7$, A$_8$, R$_3$ and R$_4$ are independently a hydrogen atom; a C$_{1-20}$ linear or branched alkyl group; a C$_{5-20}$ cycloalkyl group; a C$_{5-20}$ aryl group; and a C$_{5-20}$ aryl group having at least one substituent selected from the group consisting of a halogen atom, a C$_{1-10}$ halogenated alkyl group, —Si(R)(R')(R"), a C$_{1-10}$ alkyl group, a C$_{1-10}$ alkoxy group, a C$_{6-10}$ aryl group, a C$_{4-10}$ heteroaryl group and —N(R)(R'), at least one selected from the group consisting of A$_1$ and A$_2$, A$_2$ and A$_3$, A$_3$ and A$_4$, A$_5$ and A$_6$, A$_6$ and A$_7$, and A$_7$ and A$_8$ being interconnected, respectively; and R, R' and R" are independently selected from the group consisting of a hydrogen, a C$_{1-10}$ alkyl group, a C$_{1-10}$ alkoxy group, a C$_{6-10}$ aryl group and a C$_{4-10}$ heteroaryl group.

4. The biphenyl derivative of claim 1, wherein in formula 1, —N(Ar$_1$)(Ar$_2$) and/or —N(Ar$_3$)(Ar$_4$) are independently a group represented by formula 3:

<Formula 3>

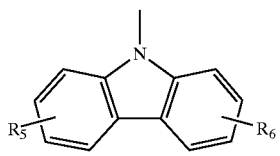

<Formula 4>

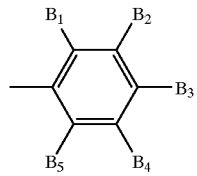

wherein $R_5$ and $R_6$ are independently a hydrogen; a $C_{1-20}$ linear or branched alkyl group; a $C_{5-20}$ cycloalkyl group; a $C_{5-20}$ aryl group; and a $C_{5-20}$ aryl group having at least one substituent selected from the group consisting of a halogen atom, a $C_{1-10}$ halogenated alkyl group, —Si(R)(R')(R''), a $C_{1-10}$ alkyl group, a $C_{1-10}$ alkoxy group, a $C_{6-10}$ aryl group, a $C_{4-10}$ heteroaryl group and —N(R)(R'), R, R' and R'' being independently selected from the group consisting of a hydrogen, a $C_{1-10}$ alkyl group, a $C_{1-10}$ alkoxy group, a $C_{6-10}$ aryl group and a $C_{4-10}$ heteroaryl group.

5. The biphenyl derivative of claim 4, wherein in formula 3, $R_5$ and $R_6$ are independently a group represented by formula 4:

wherein $B_1$, $B_2$, $B_3$, $B_4$ and $B_5$ are independently a hydrogen; a $C_{1-20}$ linear or branched alkyl group; a $C_{5-20}$ cycloalkyl group; a $C_{6-20}$ aryl group; and a $C_{6-20}$ aryl group having at least one substituent selected from the group consisting of a halogen atom, a $C_{1-10}$ halogenated alkyl group, —Si(R)(R')(R''), a $C_{1-10}$ alkyl group, a $C_{1-10}$ alkoxy group, a $C_{6-10}$ aryl group, a $C_{4-10}$ heteroaryl group and —N(R)(R'), R, R' and R'' being independently selected from the group consisting of a hydrogen, a $C_{1-10}$ alkyl group, a $C_{1-10}$ alkoxy group, a $C_{6-10}$ aryl group, and a $C_{4-10}$ heteroaryl group.

6. The biphenyl derivative of claim 1, wherein the compound represented by formula 1 is at least one selected from the group consisting of compounds represented by formulas 1a through 1e;.

<Formula 1a>

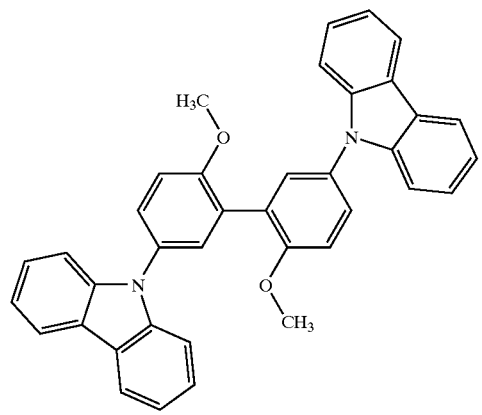

<Formula 1b>

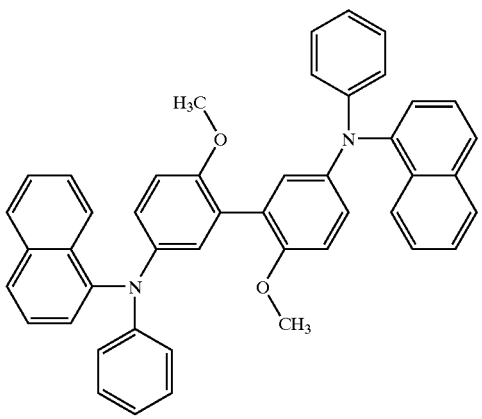

<Formula 1c>

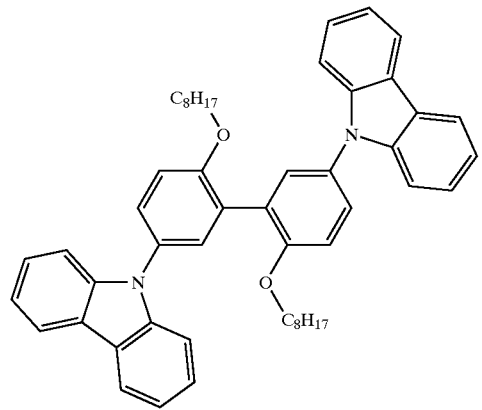

<Formula 1d>

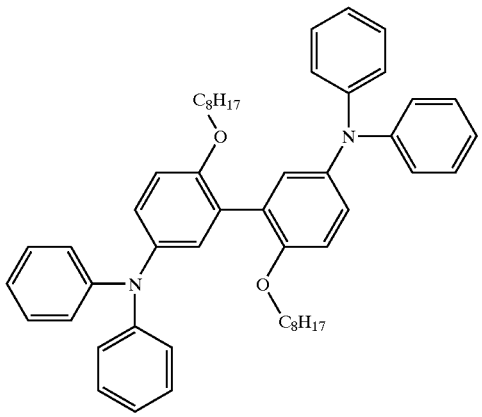

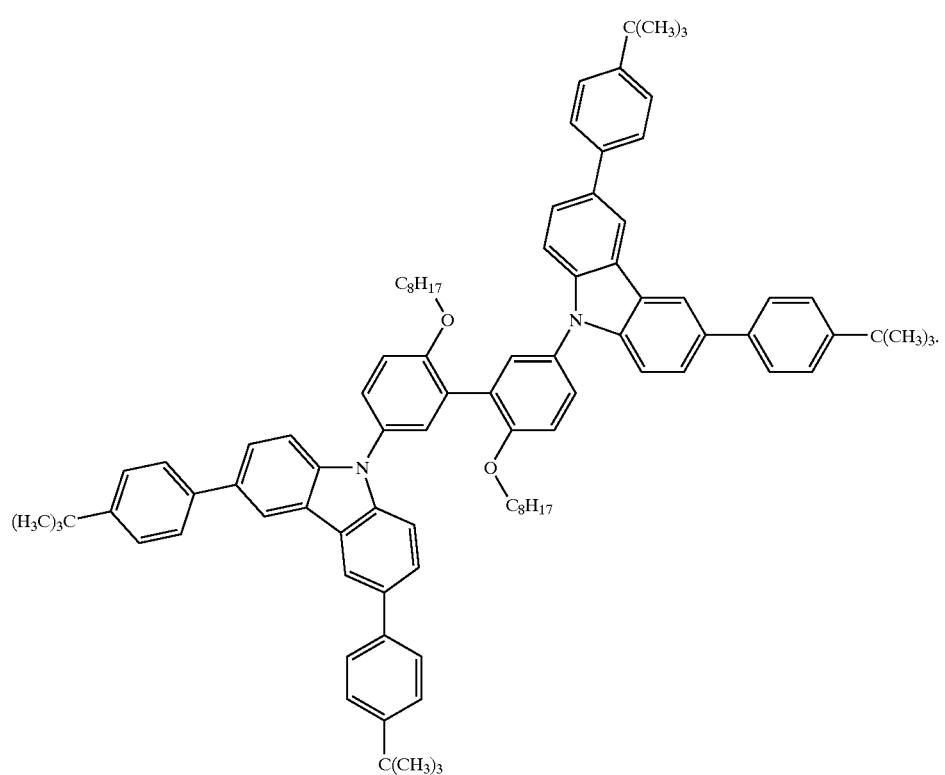

<Formula 1e>

7. An organic EL device comprising an organic layer positioned between a pair of electrodes, the organic layer containing the biphenyl derivative of any one of claims 1 through 6.

8. The organic EL device of claim 7, wherein the organic layer is an emissive layer or a hole blocking layer.

9. The organic EL device of claim 7, wherein the organic layer is an emissive layer, the emissive layer comprising 70 to 99.9% by weight of the biphenyl derivative and 0.1 to 30% by weight of a dopant.

* * * * *